(12) United States Patent
Abreu

(10) Patent No.: US 10,201,368 B2
(45) Date of Patent: Feb. 12, 2019

(54) CONTAINED TISSUE EXTRACTION DEVICE AND METHOD

(71) Applicant: Christian Abreu, Miami, FL (US)

(72) Inventor: Christian Abreu, Miami, FL (US)

( * ) Notice: Subject to any disclaimer, the term of this patent is extended or adjusted under 35 U.S.C. 154(b) by 308 days.

(21) Appl. No.: 15/167,970

(22) Filed: May 27, 2016

(65) Prior Publication Data

US 2016/0346000 A1 Dec. 1, 2016

Related U.S. Application Data

(60) Provisional application No. 62/167,971, filed on May 29, 2015.

(51) Int. Cl.
*A61B 17/3205* (2006.01)
*A61B 17/00* (2006.01)
*A61B 90/92* (2016.01)
*A61B 90/94* (2016.01)
*A61B 17/32* (2006.01)

(52) U.S. Cl.
CPC .. *A61B 17/32056* (2013.01); *A61B 17/00234* (2013.01); *A61B 90/92* (2016.02); *A61B 90/94* (2016.02); *A61B 2017/00287* (2013.01); *A61B 2017/320004* (2013.01); *A61B 2017/32006* (2013.01); *A61B 2017/320064* (2013.01)

(58) Field of Classification Search
CPC .............. A61B 17/32056; A61B 90/92; A61B 17/00234; A61B 90/94; A61B 2017/00287; A61B 2017/320064; A61B 2017/320004; A61B 2017/32006
See application file for complete search history.

(56) References Cited

U.S. PATENT DOCUMENTS

| | | | |
|---|---|---|---|
| 5,215,521 A * | 6/1993 | Cochran | A61B 17/00234 128/898 |
| 5,330,483 A * | 7/1994 | Heaven | A61B 17/00234 606/114 |
| 5,368,545 A | 11/1994 | Schaller et al. | |
| 5,611,803 A * | 3/1997 | Heaven | A61B 17/00234 606/110 |
| 5,735,289 A * | 4/1998 | Pfeffer | A61B 17/00234 600/562 |
| 5,895,392 A | 4/1999 | Riek et al. | |
| 6,537,273 B1 | 3/2003 | Sosiak et al. | |
| 8,137,372 B2 | 3/2012 | Kondoh et al. | |
| 8,282,572 B2 * | 10/2012 | Bilsbury | A61B 17/00234 600/562 |
| 8,435,237 B2 | 5/2013 | Bahney | |
| 8,795,291 B2 * | 8/2014 | Davis | A61B 17/00234 606/114 |

(Continued)

*Primary Examiner* — Phong Son H Dang
(74) *Attorney, Agent, or Firm* — H. John Rizvi; John Rizvi, P.A.

(57) ABSTRACT

A contained tissue extraction device for morcellating a tissue inside an intracorporeal cavity is disclosed. Particularly, the contained tissue extraction device includes serrated-blade wire segments that are sandwiched between an inner bag and an outer bag. The contained tissue extraction device may capture a target tissue such that a surgeon may pull the contained tissue extraction device taught through an incision that is smaller than the target tissue. The contained tissue extraction device allows a surgeon to morcellate the contained tissue by oscillating wire ends of the wire segments back and forth.

19 Claims, 20 Drawing Sheets

(56) References Cited

U.S. PATENT DOCUMENTS

| | | |
|---|---|---|
| 8,821,377 B2 | 9/2014 | Collins |
| 2004/0059345 A1* | 3/2004 | Nakao .................. A61B 17/221 606/113 |
| 2007/0016224 A1* | 1/2007 | Nakao .................. A61B 17/221 606/113 |
| 2007/0016225 A1* | 1/2007 | Nakao .................. A61B 17/221 606/114 |
| 2007/0073251 A1* | 3/2007 | Zhou ...................... A61B 10/00 604/327 |
| 2009/0192510 A1* | 7/2009 | Bahney ............ A61B 17/32056 606/45 |
| 2010/0219091 A1 | 9/2010 | Turner |
| 2011/0299799 A1* | 12/2011 | Towe ............... A61B 17/00234 383/117 |
| 2013/0131689 A1 | 5/2013 | Covidien et al. |
| 2014/0052018 A1* | 2/2014 | Hawkins ................ A61B 10/02 600/562 |
| 2016/0022352 A1* | 1/2016 | Johnson ................ A61B 18/14 606/41 |
| 2016/0296244 A1* | 10/2016 | Thomas ........... A61B 17/00234 |
| 2018/0021030 A1* | 1/2018 | Fridlin ............ A61B 17/00234 606/114 |

\* cited by examiner

CONTAINED TISSUE EXTRACTION DEVICE AND METHOD

CROSS-REFERENCE TO RELATED APPLICATION

This application claims the benefit of U.S. Provisional Patent Application Ser. No. 62/167,971, filed Jun. 29, 2015, which is incorporated herein in its entirety.

FIELD OF THE INVENTION

The present invention relates generally to surgical apparatuses, and more particularly, to a device and method for contained intracorporeal tissue extraction.

BACKGROUND OF THE INVENTION

Sometimes a surgeon may desire to remove an intracorporeal tissue. For example, a surgeon may desire to surgically remove a diseased uterus or a tumor. It is common for a surgeon to access an intracorporeal tissue via a surgical incision made through skin of a patient. It is desirable to minimize an incision size for accessing the tissue. For example, minimizing the incision size aids in reducing patient recovery time, postoperative pain, risk of infection, potential damage to surrounding organs and tissues (e.g. an incisional hernia), and blood loss. As such, minimally invasive surgery (MIS) methods may be chosen for removing diseased intracorporeal tissue.

MIS may include laparoscopic procedures that allow a surgeon to remotely operate on an intracorporeal tissue through a small incision. For example laparoscopic surgery may include operating on an intracorporeal tissue via one or two small incisions, where the target intracorporeal tissue is under direct visualization provided by remote imaging such as ultrasound or fluoroscopy imaging, or various microscopes or endoscopes.

However, it is challenging to remove intracorporeal tissue via a small incision when the subject intracorporeal tissue is much larger than an incision size for extracting the tissue. For example, uterine extraction of larger uteri through a small incision may be difficult, if not impossible. As such, it is desirable to first segment or fragment larger tissues such that smaller segments may be removed through a small incision. Such segmenting of a target tissue is known in the art as morcellation.

Various conventional methods and devices exist for providing intracorporeal tissue morcellation. For example, one common morcellation method includes manually morcellating a target intracorporeal tissue via a scalpel, scissors, or electrosurgical blade, and removing morcellated particles through a small incision via forceps or an appropriate aspirating device. Another common method includes morcellating a target intracorporeal tissue via an electromechanical morcellation (EMM) device (i.e. an electromechanical morcellator or power morcellator). Current EMM devices usually include rotating blades or cutting edges that core, peel, fragment, mince or grind a target tissue. Further, current EMM devices may include an aspirating mechanism for aspirating paste-like or fragmented tissue that result from morcellation.

However, current morcellation methods and devices have various problems. Sometimes, a target tissue may be malignant. For example, a target tissue may be a sarcoma that mimics benign myomas on preoperative imaging or screening. Morcellation of a malignant tissue may spread malignancy to other areas of a patient's body. For example, morcellating a uterine fibroid may cause malignancy or uterine fragments to spread to abdominal organs or intraperitoneal space. Current morcellation methods and devices may cause accidental morcellation of non-target tissues, which may cause severe and fatal injuries. Fatalities or severe injury from common EMM methods and devices are well known in the art, and some hospitals have banned practice of such EMM procedures. Further, current morcellation methods and devices may leave behind unretrieved or un-aspirated tissue, which may cause long term tissue fragment or malignancy dissemination. Even further, current morcellation methods and devices may morcellate a target tissue and hinder postoperative histopathological evaluation of morcellated tissue. For example, common EMM devices may grind a target tissue into a paste-like consistency, which may reduce accuracy of histopathological evaluation of the target tissue.

One solution has been implemented to solve some of the above described problems. For example, contained tissue extraction (CTE) methods may include morcellating an intracorporeal tissue inside an impermeable bag or pouch, such that target intracorporeal tissue fragments are contained in the bag, preventing undesired fragment or malignancy dissemination. However, accidentally puncturing the bag via a scalpel or EMM device during such a contained tissue extraction method still may cause tissue fragment dissemination. Further, an EMM device may still hinder postoperative histopathological evaluation of morcellated tissue. Even further, EMM devices are expensive, and surgeons or patients in less-developed countries may not be able to afford EMM methods. However, manual methods via scissors or scalpels can still puncture such contained tissue extraction bags and damage surrounding tissues or spread diseased tissue fragments.

Therefore, there exists a need for a contained tissue extraction device and method that morcellates intracorporeal tissues without causing tissue fragment dissemination or undesired damage to adjacent tissues, and extraction of large enough specimen fragments for accurate histopathological evaluation of extracted tissue.

SUMMARY OF THE INVENTION

This summary is provided to introduce a selection of concepts in a simplified form that are further described below in the detailed description. This summary is not intended to identify key features of essential features of the claimed subject matter, nor is it intended to be used to limit the scope of the claimed subject matter. Furthermore, the claimed subject matter is not limited to implementations that solve any or all disadvantages noted in any part of this disclosure.

According to embodiments of the present disclosure, a contained tissue extraction (CTE) device is disclosed, including an outer bag, an inner bag that lines the outer bag, and a set of wire segments attached to the inner bag. The set of wire segments is configured to morcellate a tissue placed inside the bag when an operator pulls on each wire segment of the set of wire segments while oscillating the ends of each wire segment back and forth.

In another aspect, each wire segment of the set of wire segments is attached to an outside of the inner bag.

In another aspect, each wire segment of the set of wire segments has a serrated-blade finish capable of cutting through a tissue.

In another aspect, each wire segment of the set of wire segments is composed of plastic or includes a plastic coating.

In another aspect, the set of wire segments is composed of metal or a metal composite.

In another aspect, the set of wire segments takes form as a set of threads.

In another aspect, the set of wire segments acts as guide wire segments such that a set of one or more cutting or morcellating wires are attached to one or both ends of each guide wire segment, and such that one end of each guide wire segment is pulled away from a mouth of the outer bag to guide the cutting or morcellating wires to engage and morcellate a tissue located inside the contained tissue extraction device.

In another aspect, the guide wire segments are configured to glide across a surface of the tissue such that the guide wire segments do not substantially cut or morcellate the tissue and such that the guide wire segments substantially grip the surface of the target tissue to glide without lateral movement or slippage.

In another aspect, the guide wire segments are configured to engage the target tissue at wire engagement routes, and said guide wire segments are pulled along said wire engagement routes to bring said cutting or morcellating wire segments to engage the target tissue at or through said engagement routes to morcellate the target tissue.

In another aspect, the set of wire segments is sandwiched between the outer bag and the inner bag.

In another aspect, the outer bag is an impermeable endoscopic bag.

In another aspect, the outer bag includes loops or other gripping elements at a bag mouth such that a surgeon may pull the bag mouth out of an intracorporeal cavity through a small incision via the loops or other gripping elements.

In another aspect, the contained tissue extraction device is configured to be folded such that it may be inserted into an intracorporeal region via a small incision.

In another aspect, the contained tissue extraction device is pulled taught through a small incision such that the outer bag tightens over a contained tissue before each wire segment is pulled out of the bag to morcellate the tissue.

In another aspect, the set of wire segments can morcellate a target tissue when the outer bag is pulled taught through the small incision, and when each wire segment is oscillated back and forth creating a frictional cutting action where each wire segment engages the target tissue.

In another aspect, the set of wire segments is attached to the inner bag such that each wire segment morcellates a target tissue one at a time in order without tangling with other wire segments.

In another aspect, each wire segment of the set of wire segments detaches from the inner bag when pulled to morcellate a target tissue located inside the contained tissue extraction device.

In another aspect, the set of wire segments has differently coded wire ends, such as color-coded, number-coded or a combination thereof, for identifying opposite ends of each wire segment and indicating an order in which each wire segment is to be pulled out for morcellating a target tissue.

In another aspect, the set of wire segments is arranged such that at least one wire segment produces a cutting or morcellating plane when pulled out of the contained tissue extraction device.

In another aspect, the morcellating plane is transverse to or intersects at least one other cutting or morcellating plane produced by one other wire segment.

In another aspect, the set of wire segments is arranged such that at least two cutting planes of the set of wire segments are not parallel one another.

In another aspect, the set of wire segments is arranged such that when the set of wire segments is viewed longitudinally from the mouth of the contained tissue extraction device, the set of wire segments has radial symmetry.

In another aspect, the set of wire segments is arranged such that when the set of wire segments is viewed longitudinally from the mouth of the contained tissue extraction device, the set of wire segments is arranged in a crosshatch pattern.

In another aspect, the set of wire segments engages the target tissue via a crosshatch engagement pattern.

Disclosed is a tissue extraction device for being introduced into an incision to an intracorporeal region and for capturing and morcellating a target tissue of the intracorporeal region, the device comprising, a non-permeable outer bag, the outer bag having a mouth, an inner bag lining the outer bag, a set of wire segments placed between the inner bag and the outer bag, the wire segments having ends that are disposed near the mouth, wherein each wire segment of the set of wire segments are arranged to be separately removable from their placement between the bags, and wherein the outer bag is tightenable around the target tissue by pulling the mouth out of the incision to a tightened configuration, and in the tightened configuration, the ends are motionable to cause the wire segments to pass through the inner bag to begin morcellating the target tissue.

In another aspect, the set of wire segments is sandwiched between the inner bag and the outer bag, the inner bag and the outer bag being glued together to form a set of pockets between the inner bag and the outer bag where the inner bag and the outer bag contact the wire segments.

In another aspect, the wire segments are loosably placed between the inner bag and the outer bag.

In another aspect, the wire segments have a serrated finish configured to saw through the target tissue when the ends are motioned back and forth in the tightened configuration.

In another aspect, the device includes a wire guide including a barrel, the barrel configured to receive one or more ends of the wire segments such that the wire segments may be threaded through the bore before being motioned.

In another aspect, the device further comprises a mesh bag between the wire segments and the inner bag, the mesh configured to collapse and compress the target tissue when a drawstring of the mesh bag is pulled.

In another aspect, the wire segments include a tissue abrasive snag configured to cut the target tissue.

In another aspect, the wire segments are smooth.

In another aspect, the device further comprises indicators for indicating a sequence in which the ends of the wire segments are to be motioned to morcellate the target tissue.

In another aspect, the device further comprises a protective sleeve disposed between the wire segments and the outer bag.

Further disclosed is a method of morcellating a tissue of an intracorporeal cavity, the method comprising, capturing the tissue in a contained tissue extraction bag, the bag including an inner bag, an outer bag, and a set of morcellating wires placed between the inner bag and the outer bag, wherein ends of the morcellating wires are placed near a mouth of the tissue extraction bag, pulling the mouth through an incision of the intracorporeal cavity to cause the extraction bag to tighten over the tissue, and while keeping the extraction bag tight over the tissue, motioning the morcellating wires to morcellate the tissue inside the bag.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the claimed subject matter will hereinafter be described in conjunction with the appended drawings provided to illustrate and not to limit the scope of the claimed subject matter, where like designations denote like elements, and in which:

It is to be understood that like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
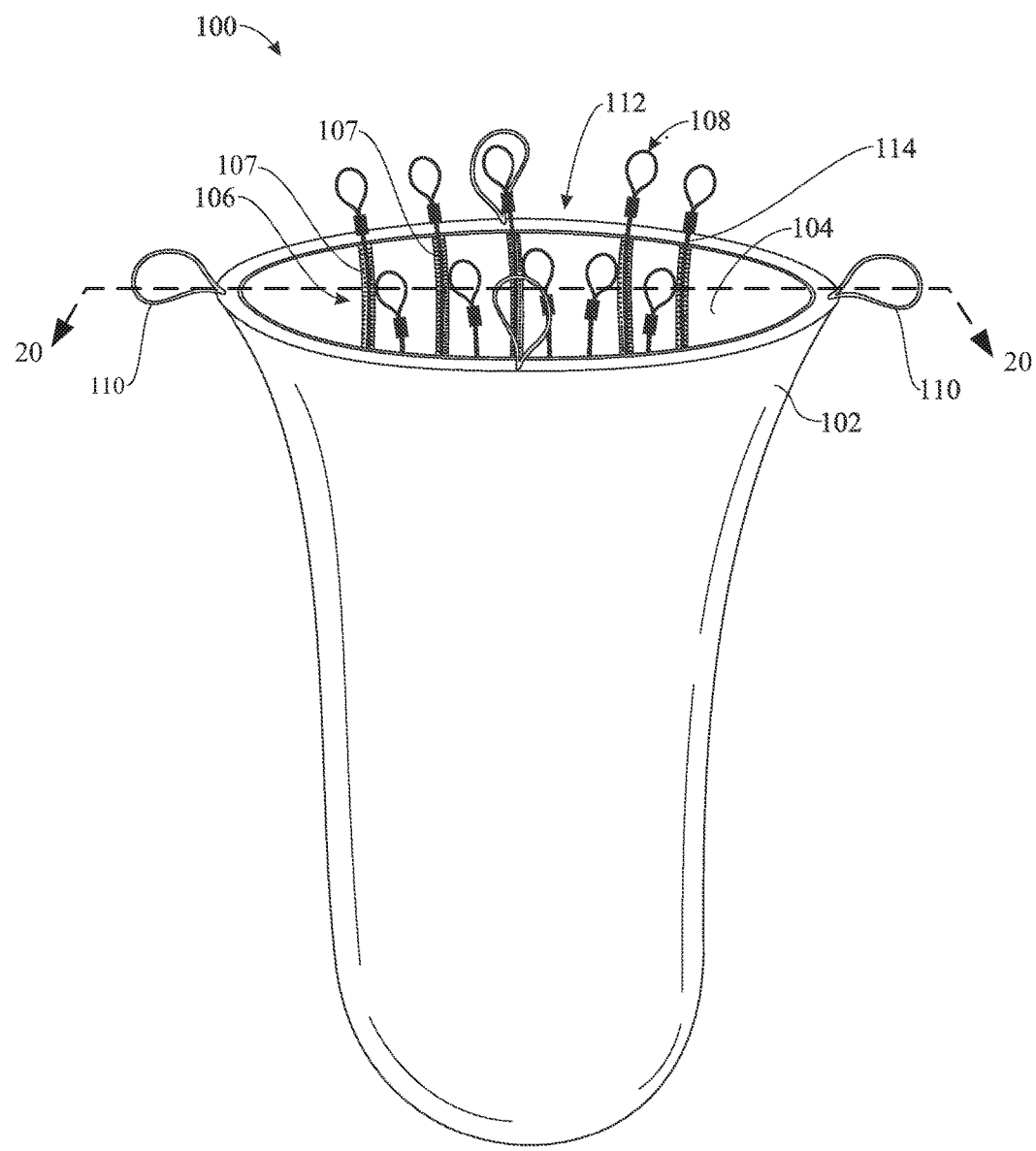
FIG. 1 presents a perspective view of a first exemplary embodiment of a contained tissue extraction (CTE) device, in accordance with aspects of the invention.

The illustrations of FIGS. 1-12 show a first embodiment of a contained tissue extraction (CTE) device in accordance with aspects of the present disclosure. For example, FIG. 1 shows an assembled contained tissue extraction device 100, including an outer bag 102, an inner bag 104, a set of wire segments 106, having wire ends 108, and outer bag loops 110. Outer bag 102 is a bag that may be introduced into an intracorporeal cavity of a mammalian body without damaging tissues. For example, outer bag 102 may be an endoscopic bag known in the art of tissue extraction. Outer bag 102 includes an impermeable membrane or layer such that tissue fragments do not pass through the impermeable membrane. Set of wire segments 106 is attached to inner bag 104 such that the wire ends 108 may extend past outer bag mouth 112. Set of wire segments 106 may be attached to an inside or an outside of inner bag 104. For example, set of wire segments 106 may be glued on to an outside of inner bag 104, such that when inner bag 104 is placed inside, or lines, outer bag 102, set of wire segments 106 is sandwiched between inner bag 104 and outer bag 102. As another non limiting example, the set of wire segments 106 may embedded into inner bag 104 such as by having the inner bag 104 made of several layers and having the set of wire segments 106 sandwiched between the several layers of inner bag 104 or by having the set of wire segments 106 embedded within a wall of the inner bag 104. Inner bag 104 can provide structure to the set of wire segments 106 such that a target tissue may be placed within the contained tissue extraction device. For example, the set of wire segments 106 may provide material tension to the inner bag 104 to aid in unfolding the contained tissue extraction device 100 for introducing a target tissue, such as target tissue 800. It is to be understood that the various bags described herein may be also invariably referred to as layers (e.g. in cross-section). It is to be understood that the wire segments may run from a first point on the mouth to an opposite second point of the mouth (e.g. each wire end may be disposed on opposite sides of the mouth, while the wire segments remain parallel with one another).

Figure 3:
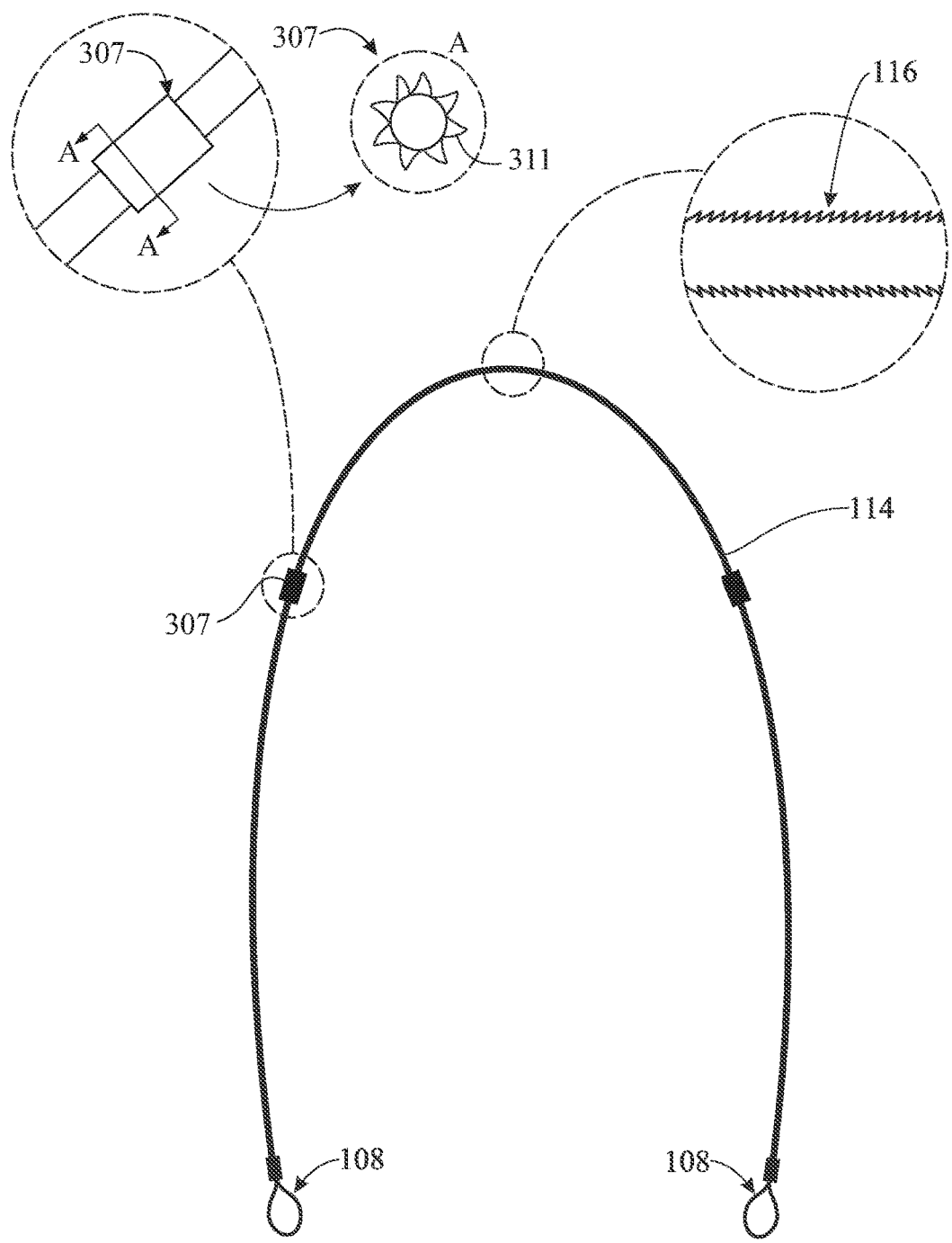
FIG. 3 presents a side view of a morcellator wire in accordance with aspects of the invention.

The illustration of FIG. 3 shows an exemplary wire segment 114 of the set of wire segments 106. Wire segment 114 is configured to morcellate a target tissue. For example, wire segment 114 is shown having a serrated-blade finish 116. Set of wire segments 106 may be arranged in a particular way to provide morcellation. For example, the set of wire segments 106 may be arranged in between inner bag 104 and outer bag 102 such that a target tissue may slide into the contained tissue extraction device 100 without getting caught on the set of wire segments 106. Inner bag 104 may be composed of material that may be cut by the set of wire segments 106 upon morcellation action. For example, a morcellation action may be a saw-like or frictional motion applied to a target tissue via each wire segment of the set of wire segments 106. Further, outer bag 102 may be composed of material that is resistant to cutting forces applied by the set of wire segments 106. As such, upon morcellation as described herein, each wire segment of the set of wire segments 106 cuts, slices or rips or is forcible through inner bag 104 to engage target tissue 800 without damaging surrounding tissues outside the contained tissue extraction device 100. In other words each wire segment of the set of wire segments 106 detach from the inner bag 104 to morcellate target tissue 800.

The set of wire segments 106 may be composed of any appropriate material. For example, the set of wire segments 106 may be composed of plastic (e.g they may be thin nylon wires) or include a plastic coating. As another example, the set of wire segments 106 may be composed of a metal. Any appropriate combination of metal, plastic, polymer or composite material may compose the set of wire segments 106. As another example, the set of wire segments 106 may take form as a set of threads having any appropriate gauge.

The illustrations of FIGS. 7-12 show an exemplary sequence of use of a contained tissue extraction device in accordance with aspects of the present disclosure.

Figure 7:
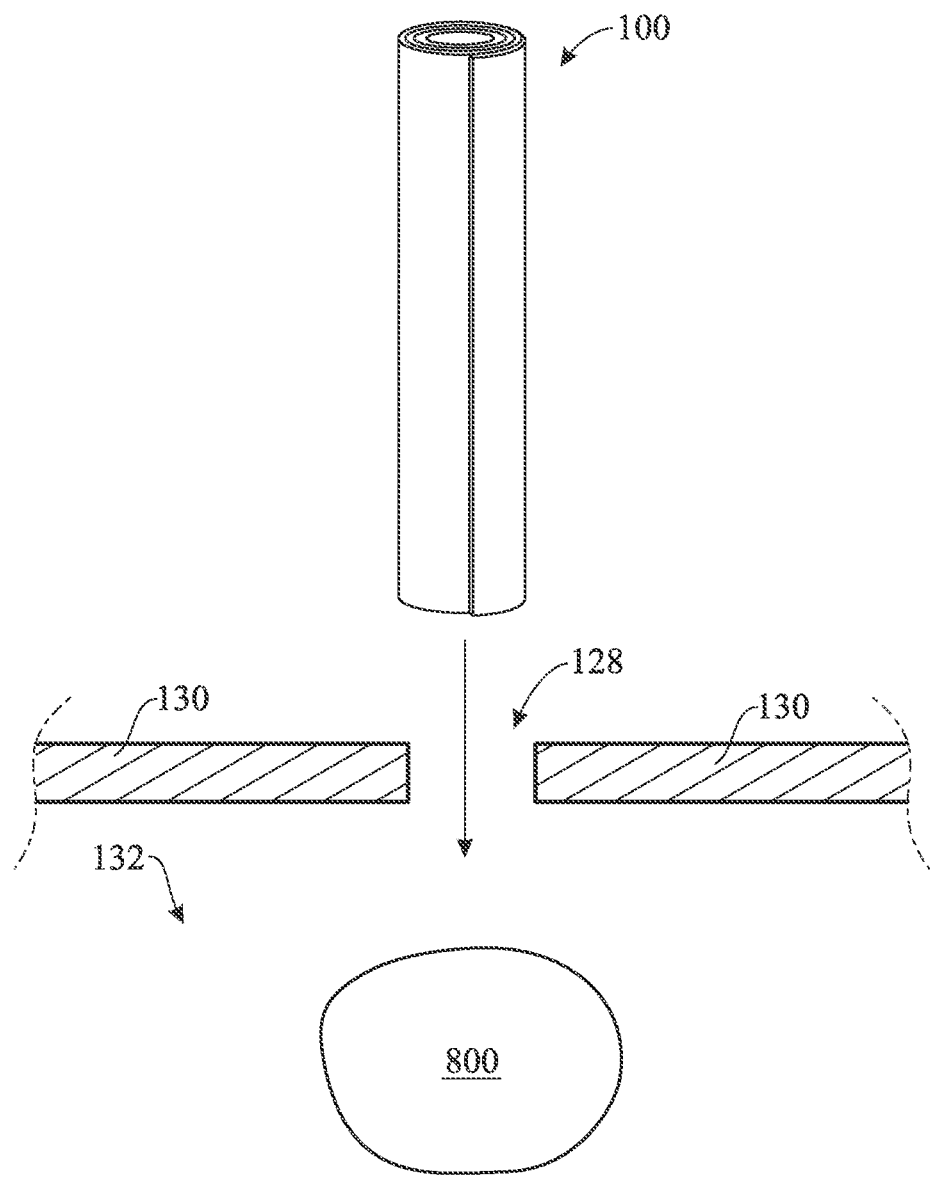
FIG. 7 presents a side view of a first step for morcellating a target tissue, where the contained tissue extraction device is being introduced into an intracorporeal cavity, in accordance with aspects of the invention.

The illustration of FIG. 7 shows a first step of an exemplary method for morcellating a target tissue 800 via the contained tissue extraction device 100. Particularly, the contained tissue extraction device 100 is shown in a folded configuration, being introduced through a small incision 128 of skin 130 into intracorporeal cavity 132 where a target tissue lies. The folded configuration may be a fan-fold of the contained tissue extraction device 100 of FIG. 1, such that the contained tissue extraction device 100 may be inserted though incision 128 without damaging adjacent tissues. Alternatively as shown in the drawing, the contained tissue extraction device 100 may be rolled up to be inserted through incision 128. Target tissue 800 may be a diseased uterus or tumor that has been detached, but that still lies inside intracorporeal cavity 132.

Figure 8:
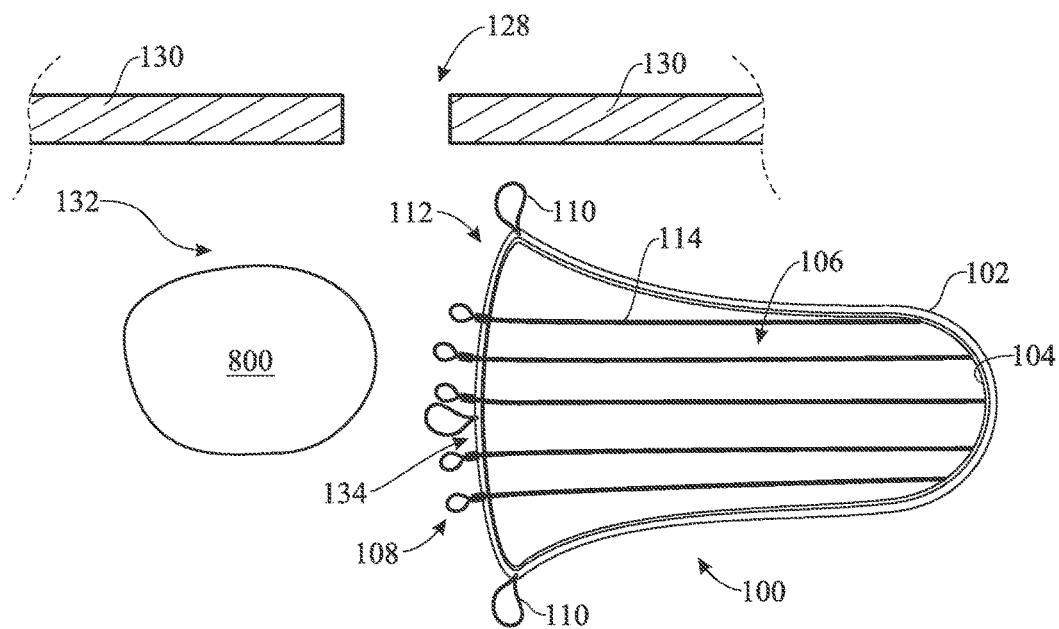
FIG. 8 presents a cross sectional side view of a second step for morcellating a target tissue, where the contained tissue extraction device has been fully introduced into the intracorporeal cavity of FIG. 7, in accordance with aspects of the invention.

The illustration of FIG. 8 shows a second step for morcellating a target tissue via the contained tissue extraction device 100. Particularly, the contained tissue extraction device 100 is shown in FIG. 8 having been unfolded in intracorporeal cavity 132, such that the target tissue 800 may be introduced into the contained tissue extraction device 100 through a contained tissue extraction device mouth 134. For example, a surgeon may maneuver outer bag loops 110 to introduce the target tissue 800 into the contained tissue extraction device 100. A surgeon may also choose to maneuver the target tissue 800 into contained tissue extraction device 100. Maneuvering outer bag loops 110 may be accomplished via another incision or via a trocar device that allows a surgeon to operate manipulative tools through the same incision 128. Any appropriate tool may be used to manipulate the contained tissue extraction device 100 or the target tissue 800 to introduce the target tissue into the contained tissue extraction device. It is to be understood that any loops described herein may take form as any appropriate gripping structure.

Figure 9:
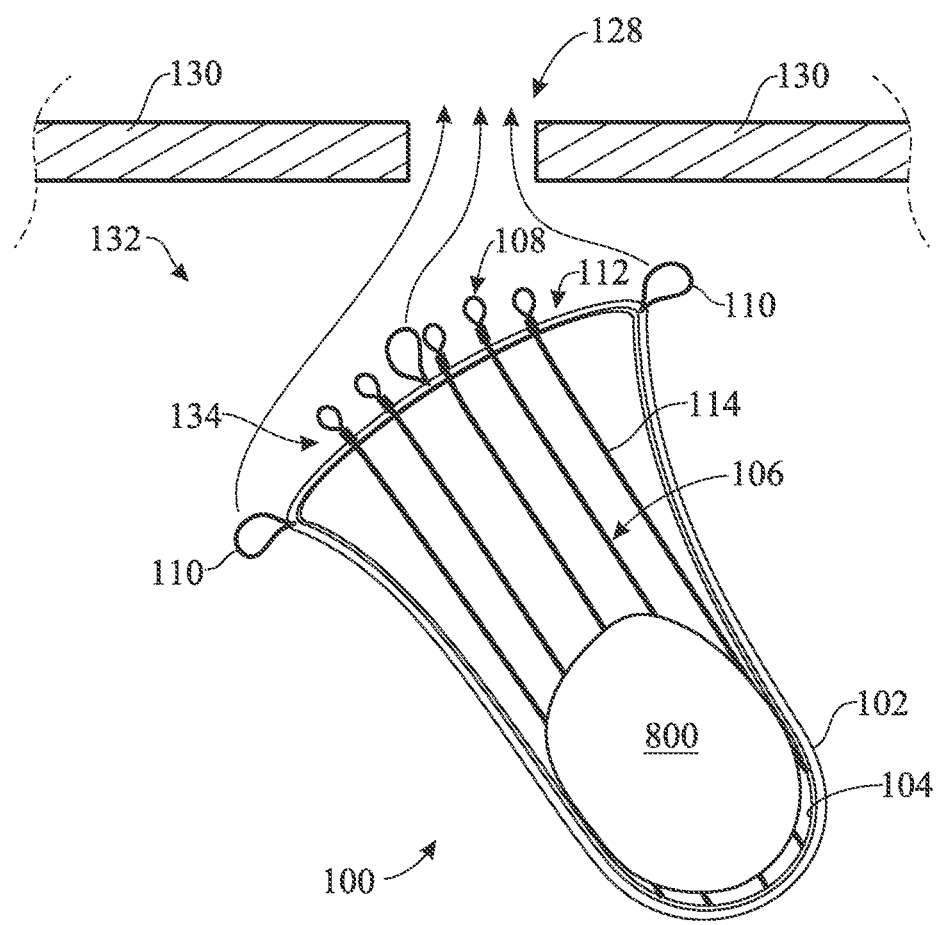
FIG. 9 presents a cross sectional side view of a third step for morcellating a target tissue, where the target tissue has been fully introduced into the contained tissue extraction device and where an opening of the contained tissue extraction device is being pulled out towards an incision in skin that covers the intracorporeal cavity, in accordance with aspects of the invention.

The illustration of FIG. 9 shows a third step for morcellating a target tissue using the contained tissue extraction device 100, where the contained tissue extraction device 100 is being drawn via outer bag loops 110 toward incision 128, after the target tissue 800 has been captured inside contained tissue extraction device 100. Although not shown in the drawings, the contained tissue extraction device 100 may include a drawstring to pull the contained tissue extraction device mouth 134 close to or out of incision 128.

Figure 10:
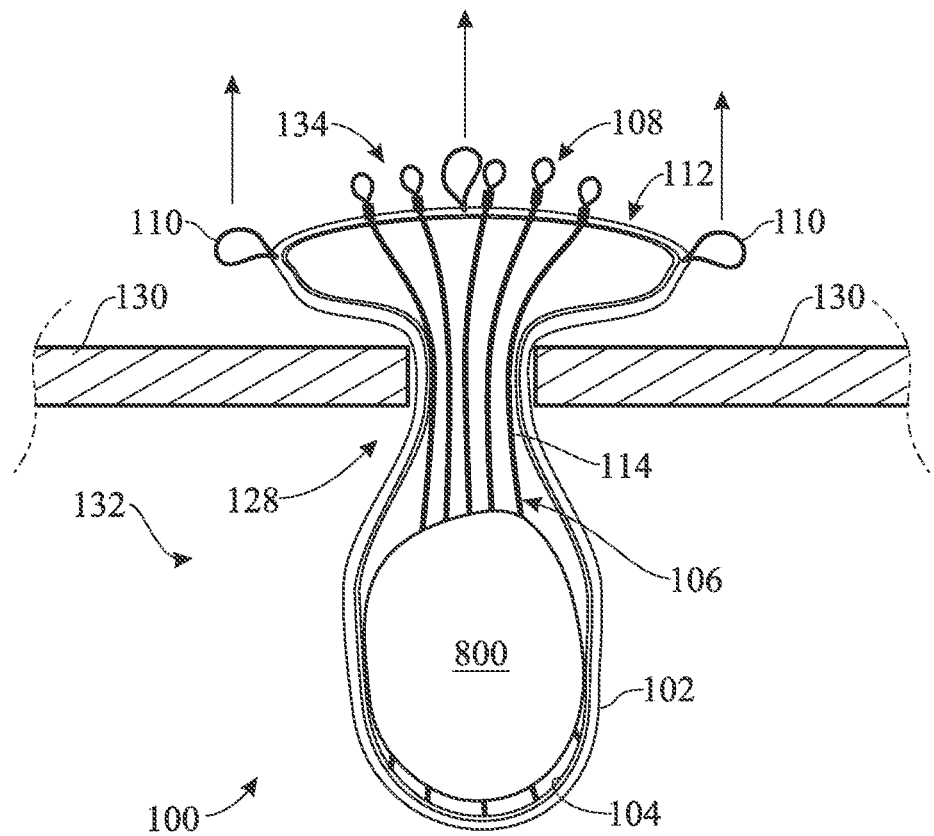
FIG. 10 presents a cross sectional side view of a fourth step for morcellating a target tissue, where the opening of the contained tissue extraction device has been fully pulled out of the intracorporeal cavity, in accordance with aspects of the invention.

The illustration of FIG. 10 shows a fourth step for morcellating a target tissue using the contained tissue extraction device 100, where the contained tissue extraction device mouth 134 has been pulled through incision 128, such that contained tissue extraction device mouth 134, outer bag loops 110, and wire ends 108 are disposed outside the intracorporeal cavity 132.

Figure 11:
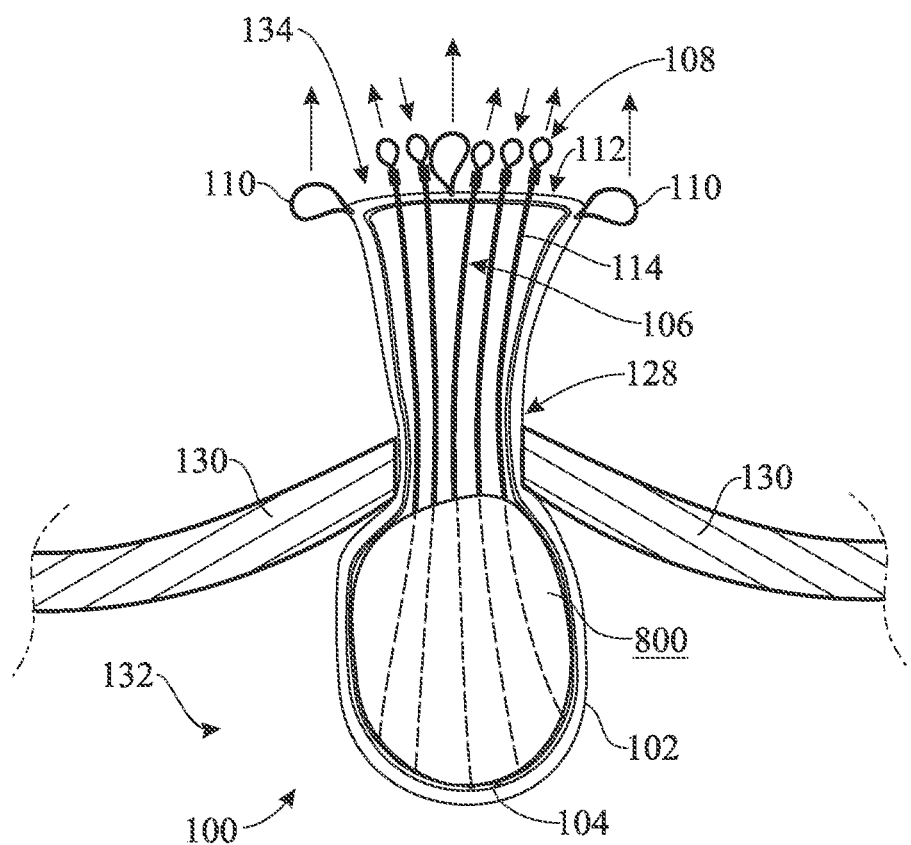
FIG. 11 presents a cross sectional side view of a fifth step for morcellating a target tissue, where wire segments of the tissue extraction device morcellate a target tissue, in accordance with aspects of the invention.

The illustration of FIG. 11 shows a fifth step for morcellating a target tissue using the contained tissue extraction device 100, where outer bag loops 110 are being pulled taught (e.g. being tightenable) through incision 128. For example, the target tissue 800 is larger than incision 128 and cannot be completely pulled out of incision 128 without damaging tissue around the incision, such as skin 130. As such, when outer bag loops 110 are pulled, walls of incision 128 form a bottle-neck inside outer bag 102 providing tension to outer bag 102 and to the set of wire segments 106, and a squeezing force to target tissue 800. Particularly, FIG. 11 shows force applied to outer bag loops 110 to apply tension on the set of wire segments 106. Once appropriate force is administered to outer bag loops 110 to keep the contained tissue extraction device 100 taught (tightened configuration), wire ends 108 of each wire segment may be oscillated (e.g. longitudinally oscillated) as described below with respect to FIG. 4. The illustration of FIG. 11 shows wire ends 108 of each wire segment being concurrently oscillated and pulled out of incision 128. As such, target tissue 800 becomes morcellated inside intracorporeal cavity 132, with morcellating cuts shown in dashed line.

Figure 4:
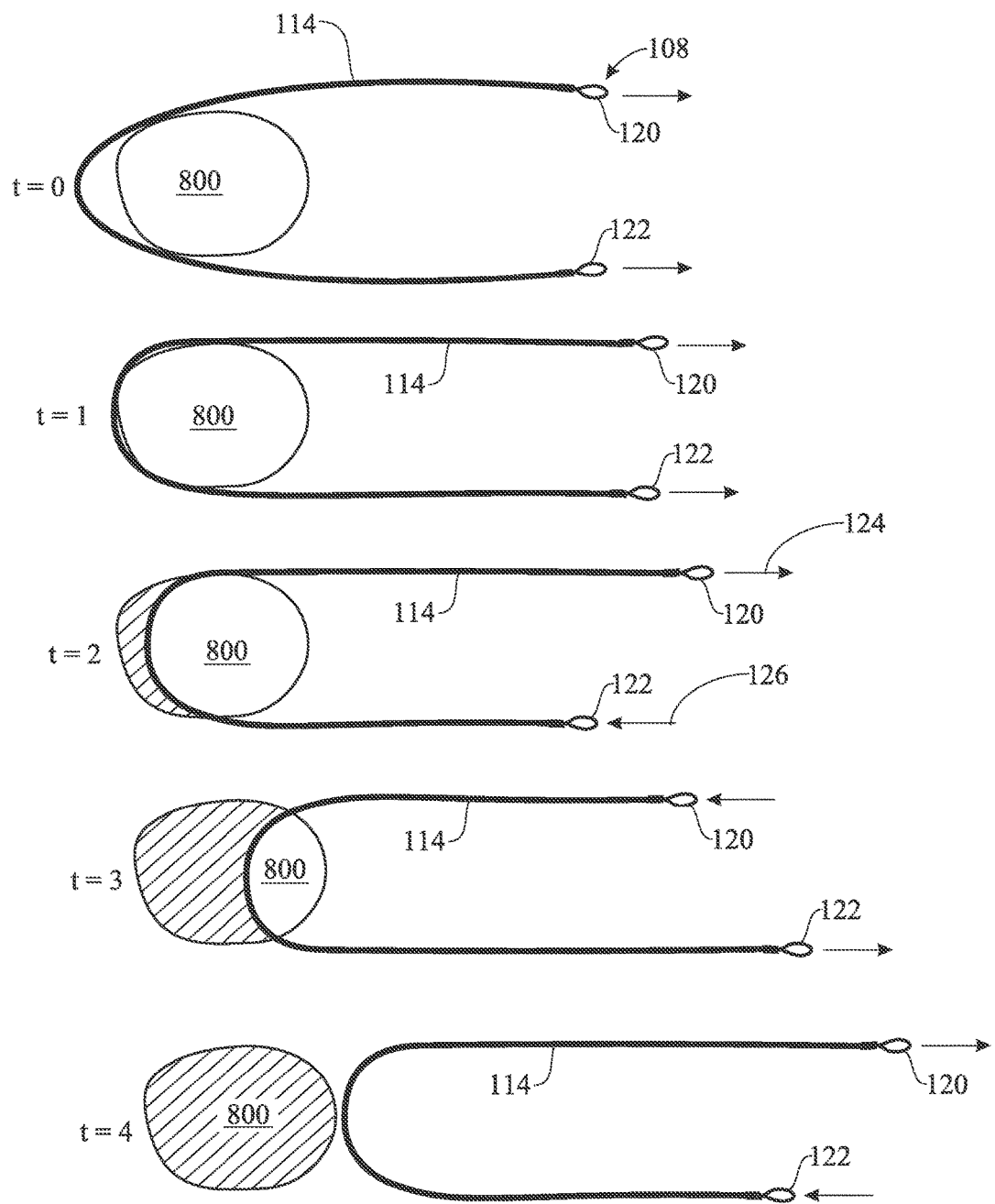
FIG. 4 presents a side view of the morcellator wire of FIG. 4 morcellating a tissue in accordance with aspects of the invention.

The illustration of FIG. 4 shows a wire segment 114 of the set of wire segments 106 morcellating a target tissue 800. Wire segment 114 is shown in FIG. 4 morcellating target tissue 800 by oscillating pulling force magnitudes delivered to first wire end 120 and second wire end 122 of wire segment 114. For example, at time t=0, wire segment 114 is being brought to engage target tissue 800 by pulling first wire end 120 and second wire end 122 in a same direction. At time t=1, wire segment 114 is pulled via wire end 120 and wire end 122 to engage target tissue 800 such that wire segment 114 substantially grips target tissue 800. At time t=2, first wire end 120 is pulled as indicated by first arrow 124, and second wire end 122 is slightly released as indicated by second arrow 126. In other words, first wire end 120 is translated away from target tissue 800 and second wire end 122 is translated toward target tissue 800 while keeping wire segment 114 under significant tension to keep wire segment 114 engaged with target tissue 800, causing wire segment 114 to begin cutting target tissue 800. At time t=3, second wire end 122 is translated away from target tissue 800 and first wire end 120 is translated toward target tissue 800, further cutting target tissue 800, while keeping wire segment 114 taught thus causing the wire to cut through the target tissue 800. At time t=4, target tissue 800 has been morcellated as wire segment 114 has passed through target tissue 800, causing target tissue 800 to become segmented or fragmented. In other words, first wire end 120 and second wire end 122 wire are translated back and forth in an alternating (or saw-like) manner such that an engaged portion of the wire segment 114 provides a lateral or rotational cutting force via serrated-blade finish 116 while constant tension is applied to the wire segment 114, resulting in a net force pulling the wire segment 114 through target tissue 800.

Figure 5:
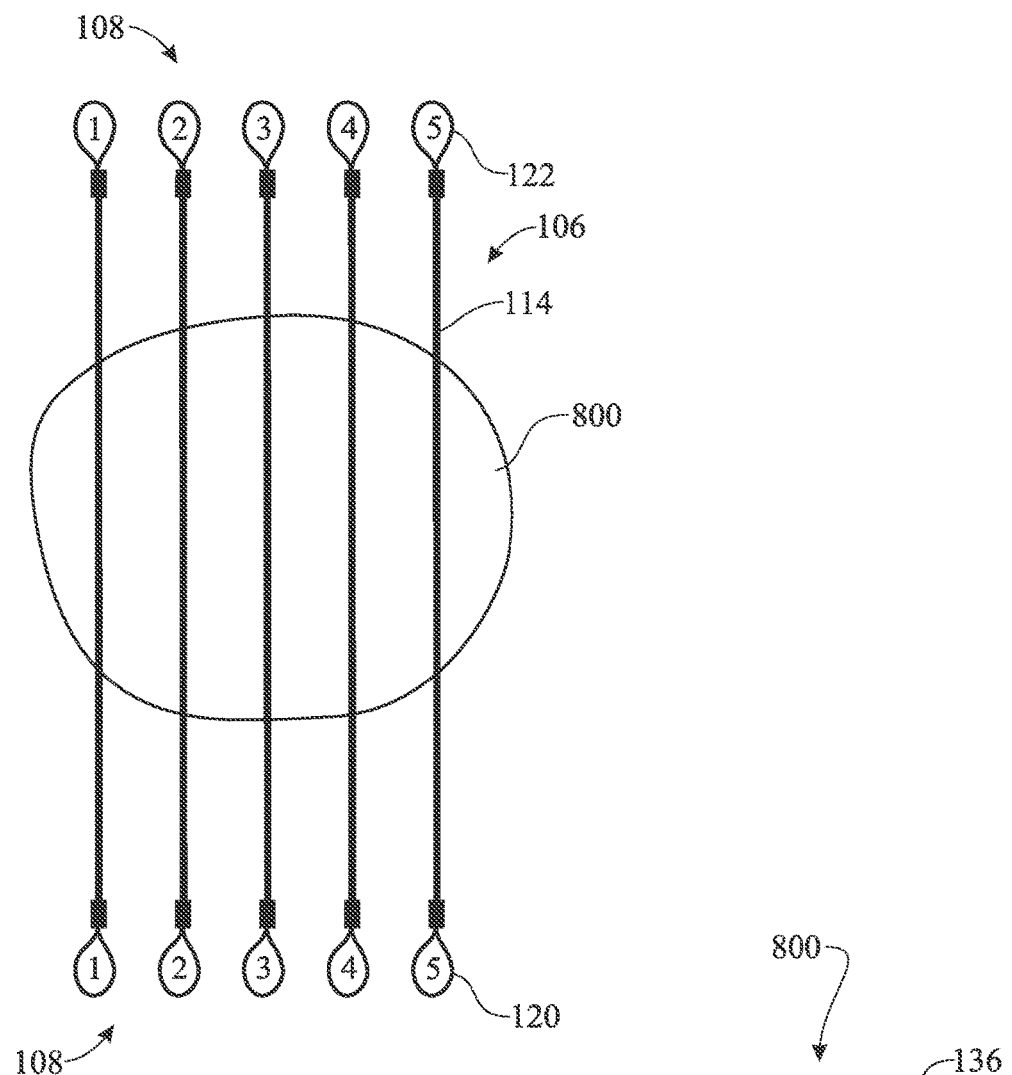
FIG. 5 presents a plan view of a plurality of morcellator wire segments engaging a tissue in accordance with aspects of the invention.

The set of wire segments 106 may be particularly arranged such that each wire segment may be removed one-by-one in sequence to properly morcellate a target tissue without each wire segment of the set of wire segments 106 becoming tangled or caught on each other. Wire ends 108 may be color coded to indicate which particular wire each wire end belongs to. For example, wire ends 120 and 122 may be color coded a same color, but wire ends of another wire segment may be color coded via a different color. Alternatively or additionally, such color coding may be configured to identify opposite ends of each wire segment and indicate the order in which each wire segment of the wire segments 106 need to be pulled or operated. The set of wire segments 106 is appropriately placed or arranged inside contained tissue extraction device 100 such that each wire segment (i.e. wire segment 114) can be pulled out of the contained tissue extraction device 100 in an order indicated by the color coding, and such that each wire segment of the set of wire segments 106 can be pulled out in order without tangling with or contacting other wire segments of the set of wire segments 106. For example, a wire segment that is to be pulled out first in order may have both wire ends 108 color coded "red", and a wire segment that is to be pulled out second in order may have both wire ends 108 color coded "blue". Alternatively, a numbering system may be used to number both wire ends 108 of exemplary wire segment 114 to indicate an order in which each wire segment of the set of wire segments 106 is to be pulled out. For example, FIG. 5 shows the set of wire segments 106 each having wire ends 108 number coded as "1", "2", "3", "4", and "5". This may indicate that the wire segment marked with "1" must be pulled out first, that the wire segment marked with "2" must be pulled out second, that the wire segment marked with "3" must be pulled out third, and so on.

Figure 6:
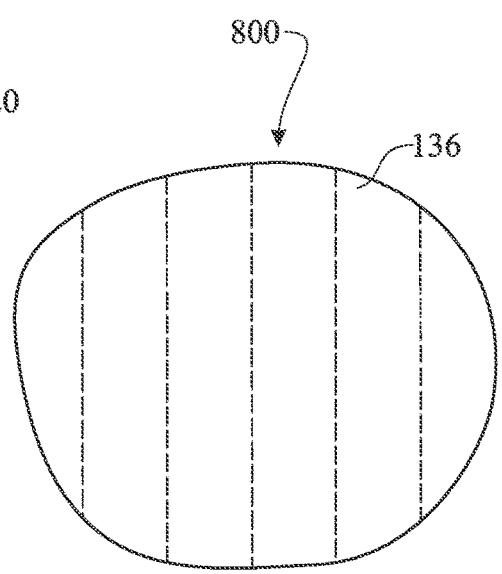
FIG. 6 presents the tissue of FIG. 5 having been morcellated by the plurality of morcellator wires in accordance with aspects of the invention.

The set of wire segments 106 may be arranged such that at least one wire segment, such as wire segment 114, produces a cutting or morcellating plane when pulled out of the contained tissue extraction device 100 while morcellating the target tissue 800. For example, FIG. 6 shows parallel cutting or morcellation planes in dashed line. As another example, the morcellating plane may be transverse to or may intersect at least one other cutting or morcellating plane produced by one other wire segment, or the set of wire segments 106 may be arranged such that at least two cutting planes of the set of wire segments 106 are not parallel to one another or are substantially perpendicular or orthogonal to one another. As yet another example, the set of wire segments 106 may be arranged such that when the set of wire segments 106 is viewed longitudinally from the mouth 134 of the contained tissue extraction device, the set of wire segments 106 has radial symmetry or has a crosshatch pattern. As such, the set of wire segments 106 may be arranged to engage the target tissue 800 via a crosshatch engagement pattern.

Each wire segment of the set of wire segments 106 may be oscillated in various ways. For example, an oscillator machine may be attached to wire ends 108, such machine appropriately oscillating each wire segment for providing morcellation of a target tissue. Alternatively, wire ends 108 may be oscillated back-and-forth manually by an experienced surgeon. In alternative embodiments, each wire segment of the set of wire segments 106 could be spiraled in a fixed direction while applying a tension, instead of serrating or moving the wires back and forth in saw-like motion as shown in FIG. 4.

The illustration of FIG. 5 shows five wire segments of the set of wire segments 106 of the present embodiment engaging the target tissue 800. Each wire segment of the set of wire segments 106 may cut or morcellate target tissue 800 as described with respect to FIG. 4. The illustration of FIG. 6 shows cuts in dashed line forming in target tissue 800 delivered by the five wire segments of the set of wire segments 106 after morcellation.

Figure 12:
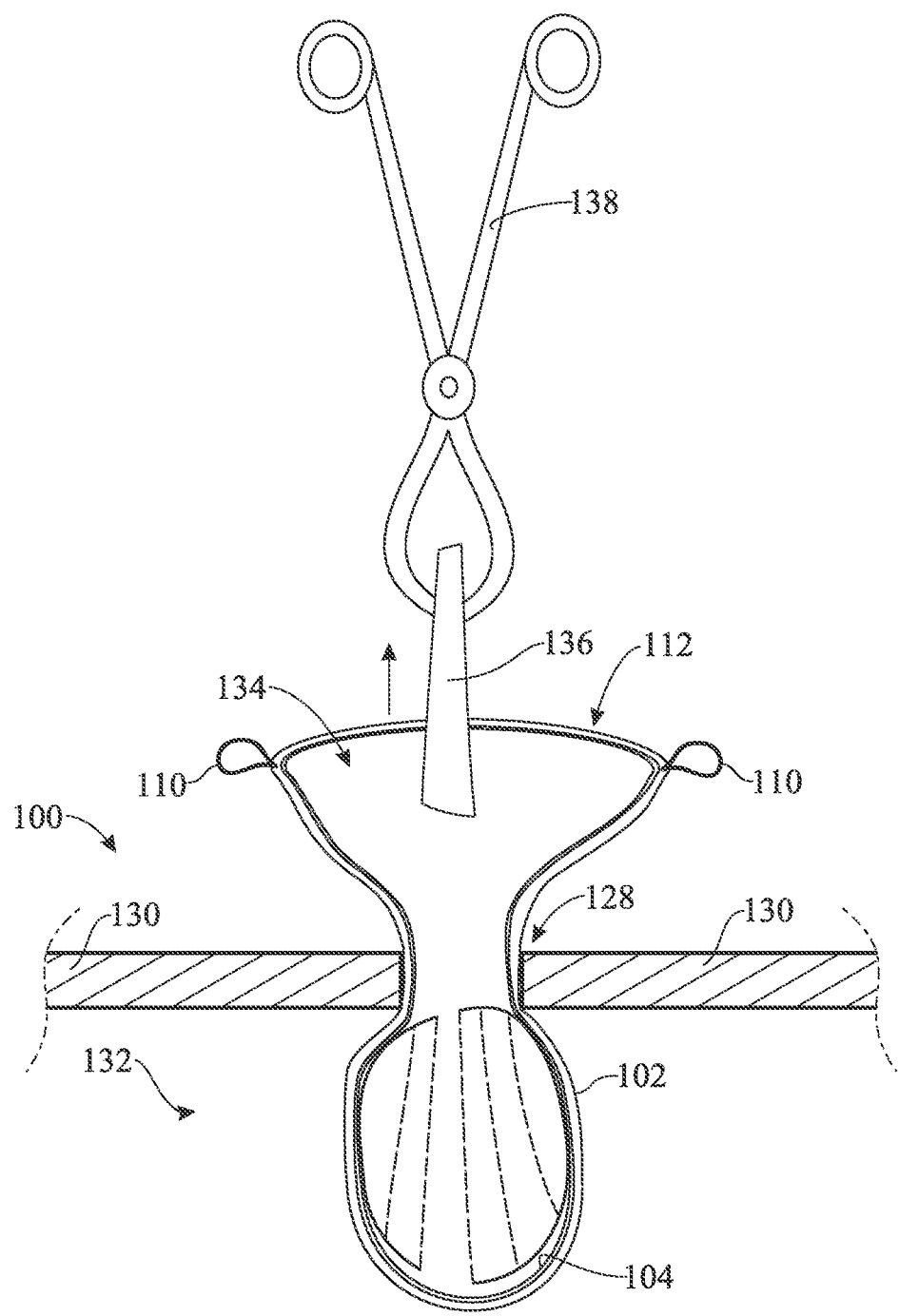
FIG. 12 presents a cross sectional side view of the intracorporeal cavity of FIG. 7, where the morcellated tissue is being removed from the contained tissue extraction device, in accordance with aspects of the invention.

Further, FIG. 12 shows a tissue segment 136 of target tissue 800 being extracted via forceps 138 after morcellation. Alternatively, after morcellation, target tissue 800 may be extracted by merely pulling outer bag 102 away and out of intracorporeal cavity 132, because after morcellation the target tissue 800 may deform to be pulled out of incision 128. Further, a vacuum device may be used to aspirate morcellated tissue.

Figure 13:
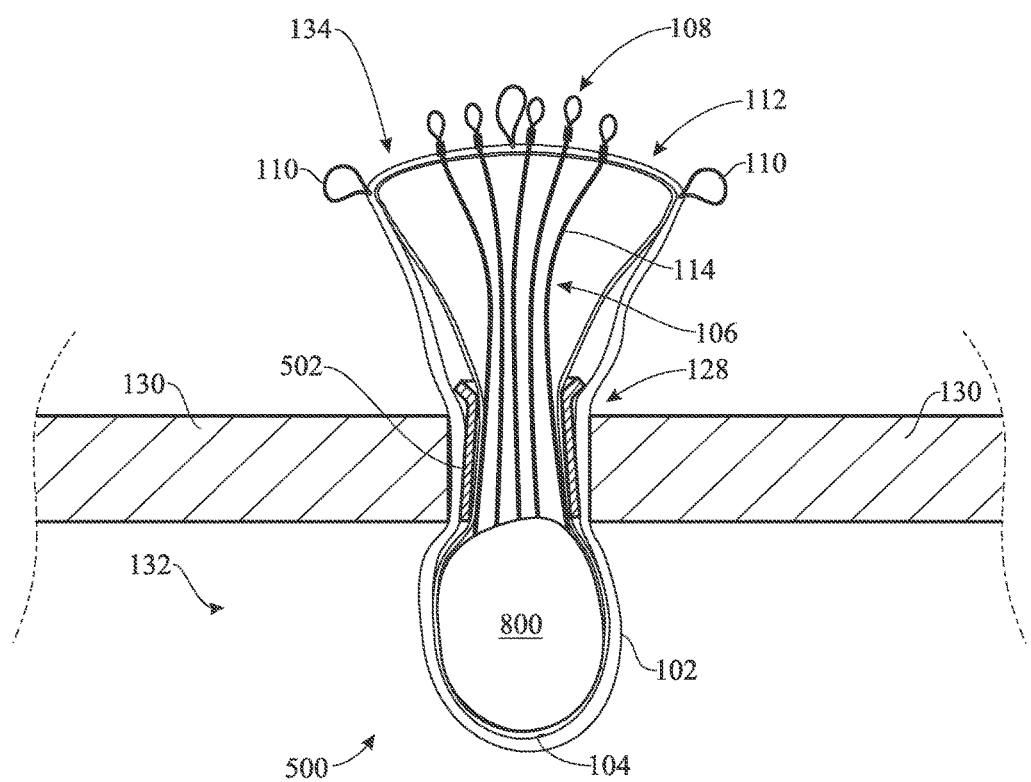
FIG. 13 presents a cross sectional side view of the intracorporeal cavity of FIG. 7, showing a second embodiment of the present disclosure including a protective structure disposed between walls of an incision and the wire segments, in accordance with aspects of the invention
Figure 14:
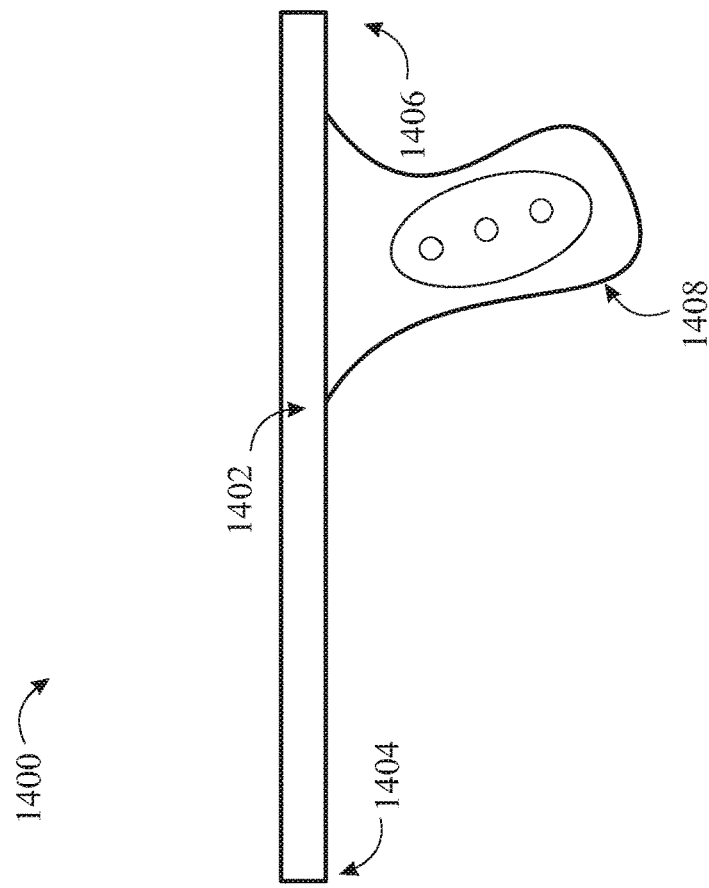
FIG. 14 presents a side view of a guide tool, in accordance with aspects of the invention.
Figure 14:
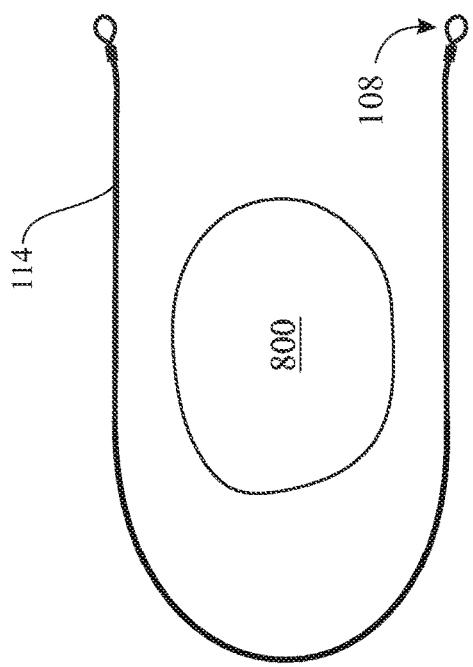
Figure 15:
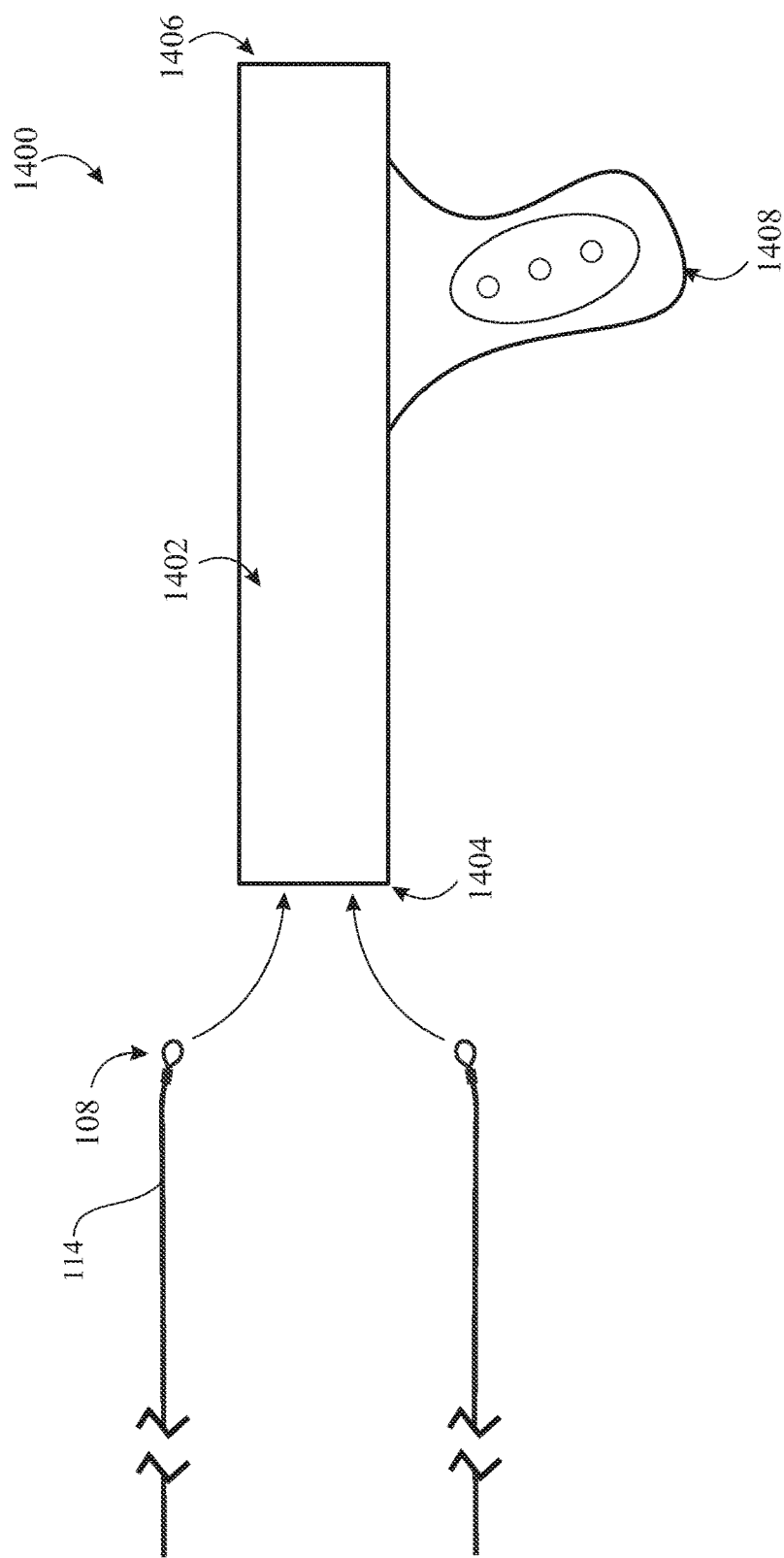
FIG. 15 presents a side view of the guide tool of FIG. 14 and an exemplary wire being motioned to be threaded through a front end of the guide tool, in accordance with aspects of the invention.
Figure 16:
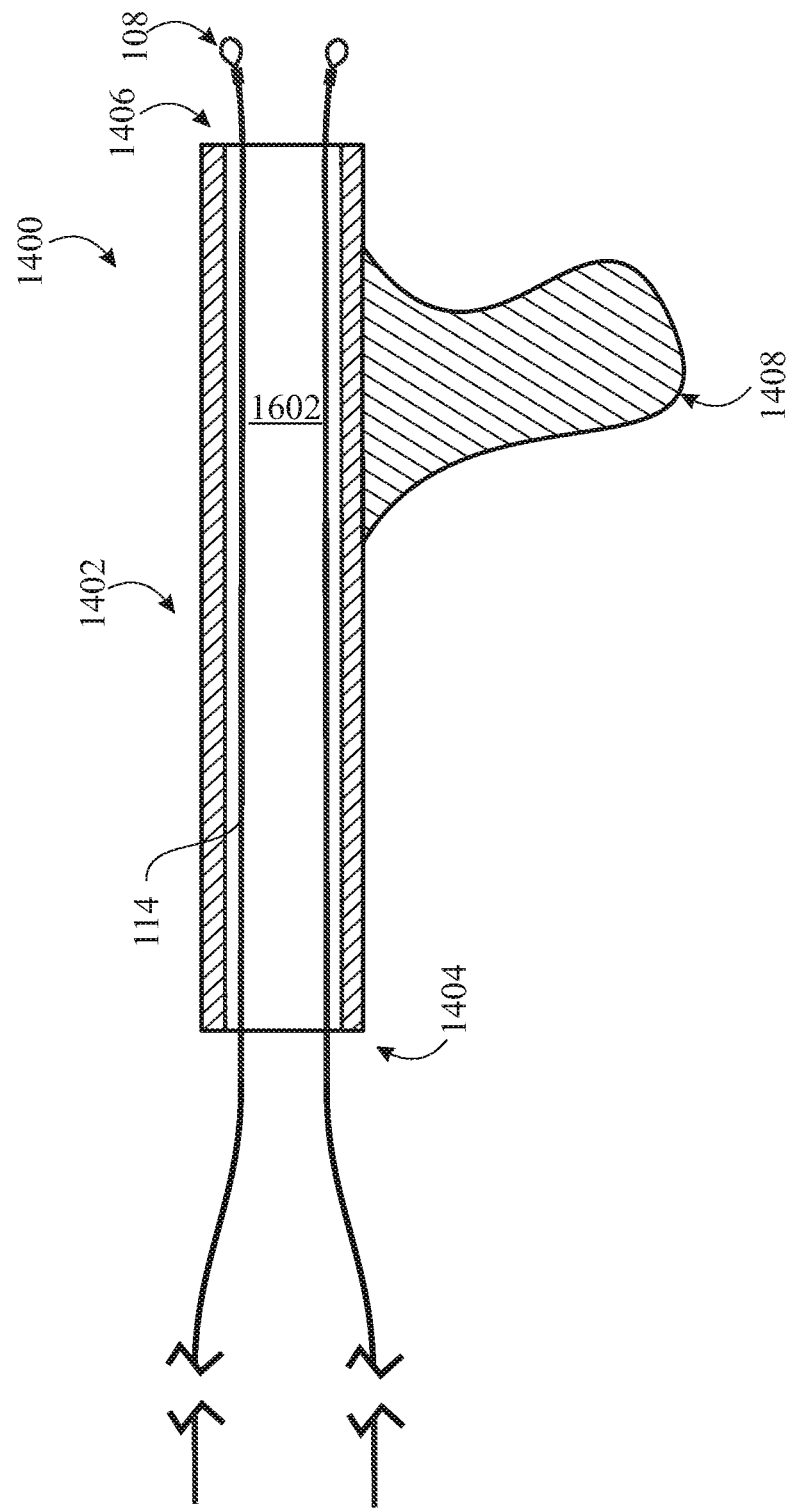
FIG. 16 presents a cross sectional side view of the guide tool, where an exemplary wire has been threaded through a bore of the guide tool, in accordance with aspects of the invention.
Figure 17:
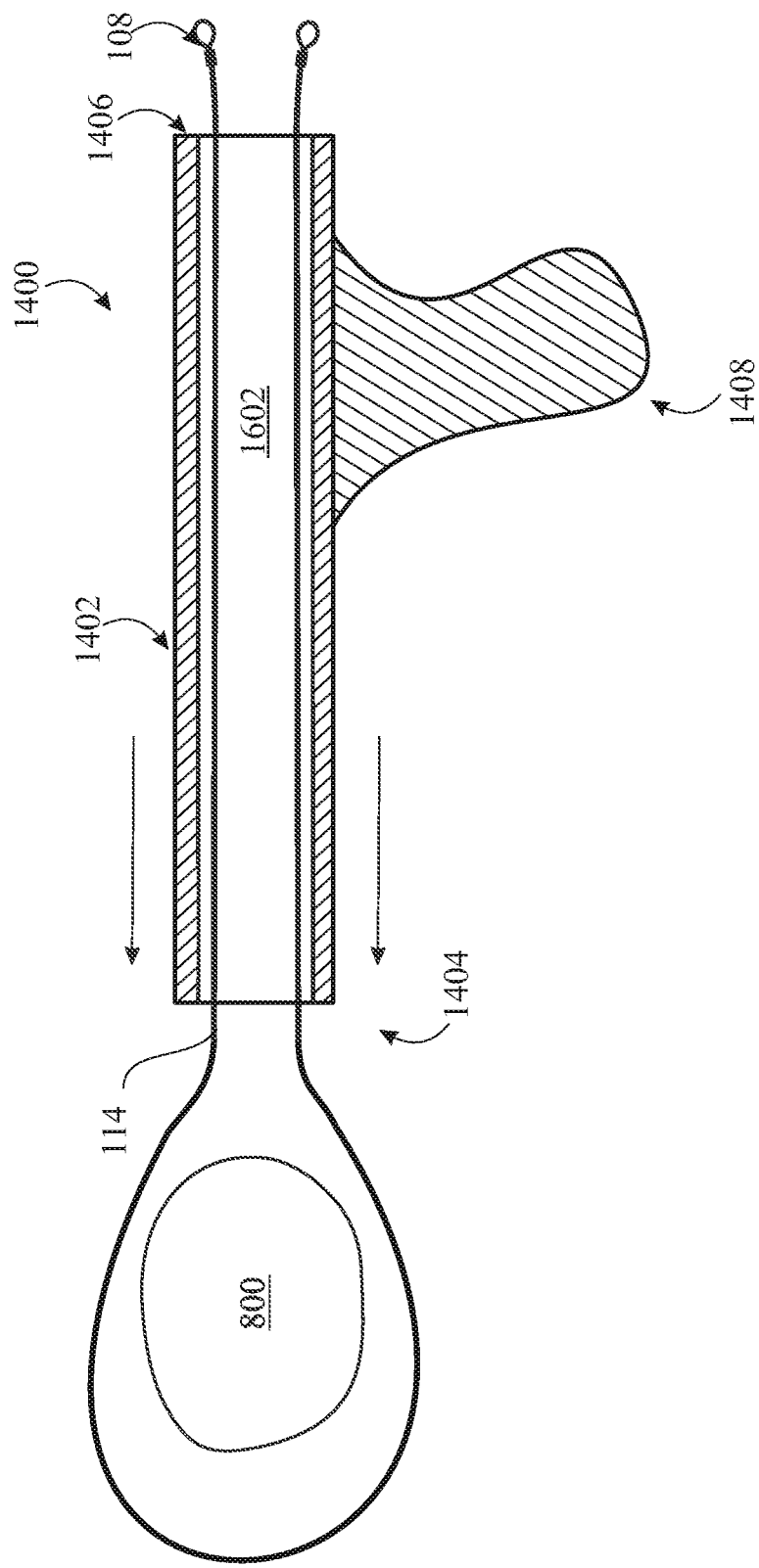
FIG. 17 presents a cross sectional side view of the guide tool, where a front end of the guide tool is being motioned toward a target tissue, in accordance with aspects of the invention.

The drawing of FIG. 13 shows a second embodiment of a contained tissue extraction device in accordance with aspects of the present disclosure. Particularly, FIG. 13 shows alternative contained tissue extraction device 500 including a protective structure 502 between outer bag 102 and the set of wire segments 106 to protect surrounding tissues during morcellation. For example, protective structure 502 may protect skin 130 or any applicable body tissue adjacent to the opening 128 when each wire segment of the set of wire segments 106 is being oscillated to morcellate target tissue 800. The protective structure 502 may be a or sleeve tube that is rigid, flexible, straight or curved or any combination thereof.

It is to be understood that the disclosed contained tissue extraction device or methods may include variations without departing from scope of this disclosure. For example, wire segment 114 may have any appropriate cutting edge for morcellating a target tissue, and may not necessarily have a serrated finish. For example, wire segment 114 may instead be thin enough to be pulled through target tissue 800 without requiring oscillative action. Wire segment 114 may have a cylindrical cross section. However, it is to be understood that wire segment 114 may have any appropriate cross section.

The contained tissue extraction device 100 and associated method may include other variations. For example, in another embodiment, the set of wire segments 106 can act as guide wire segments such that a set of one or more auxiliary cutting or morcellating wires such as wire segment 114) may be attached to one or both ends of each guide wire segment, and such that one end of each guide wire segment may be pulled or motioned away from the mouth 134 (away from the tissue) to guide the one or more auxiliary cutting or morcellating wires to engage and morcellate the tissue 800 located inside the contained tissue extraction device 100. As such, the guide wire segments may be configured to glide along a surface of the tissue 800 such that the guide wire segments do not substantially cut or morcellate the tissue 800 and such that the guide wire segments substantially grip the surface of the target tissue 800 to glide along without lateral movement or slippage. The guide wire segments may be configured to engage and travel along the surface of the target tissue 800 at or along wire engagement routes. Said guide wire segments may be pulled from one end of wire ends 108 to travel along said wire engagement routes and bring said auxiliary cutting or morcellating wire segments to engage the target tissue at or through said engagement routes to morcellate the target tissue via methods described herein.

Additionally, the contained tissue extraction device 100 may be insufflated during morcellation of the contained target tissue 800. For example, a surgeon may choose to insufflate the outer bag 102 or the inner bag 104 such that the target tissue may be properly manipulated into the contained tissue extraction device 100 without the target tissue 800 becoming caught on structural elements of the contained tissue extraction device 100. Further, a surgeon may choose to also insufflate the intracorporeal cavity 132 to properly maneuver the target tissue 800 or safely manipulate the contained tissue extraction device 100 without surrounding tissues hindering manipulation. Further still, contained tissue extraction device 100 may not need to be completely taught to start morcellating the target tissue 800. For example, outer bag 102 or inner hag 104 may be slightly loose or even insufflated while target tissue 800 is morcellated via pulling each wire segment of the set of wire segments 106 out of incision 128.

Figure 2:
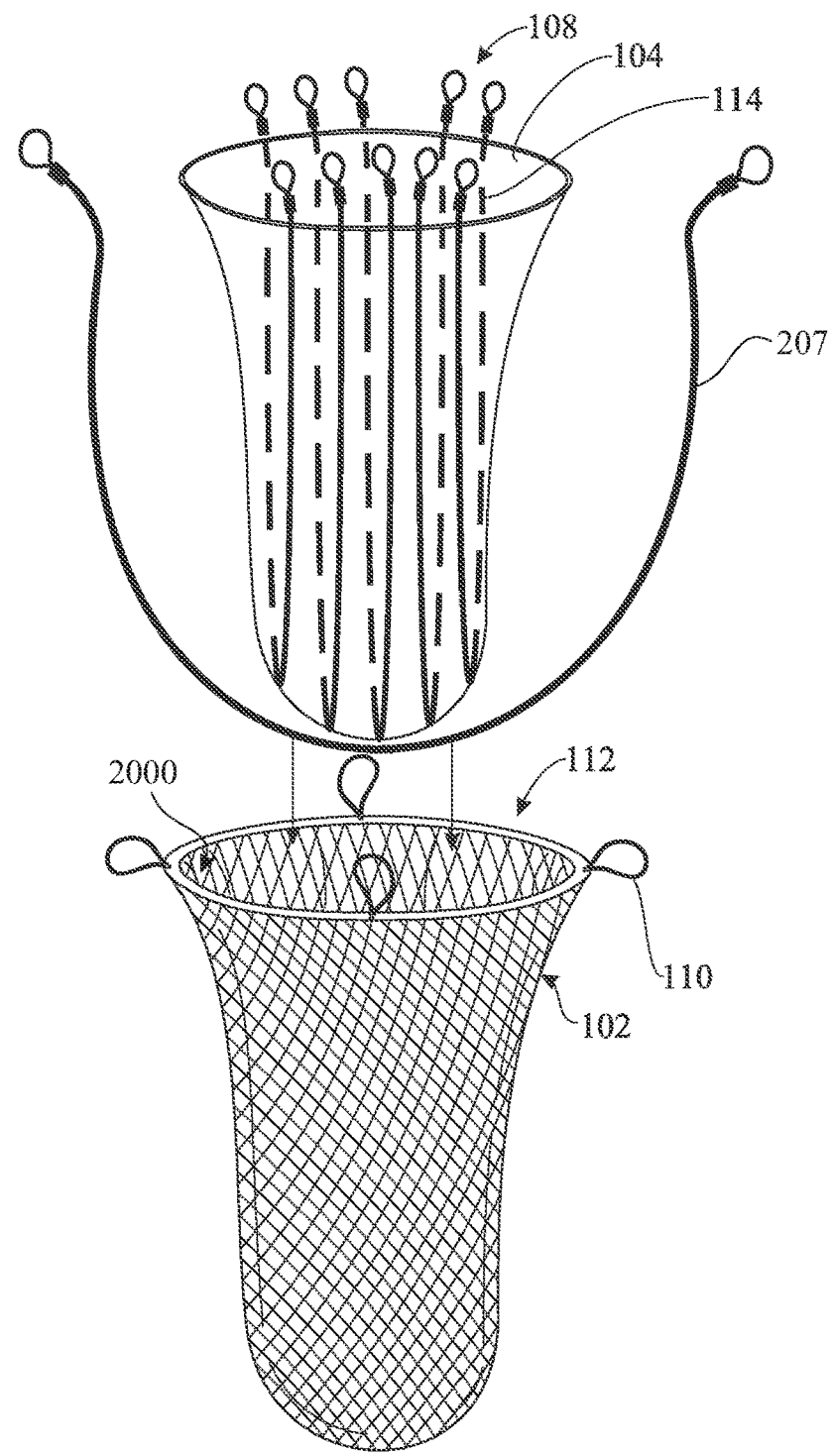
FIG. 2 presents an exploded perspective view of the contained tissue extraction device of FIG. 1 in accordance with aspects of the invention.
Figure 20:
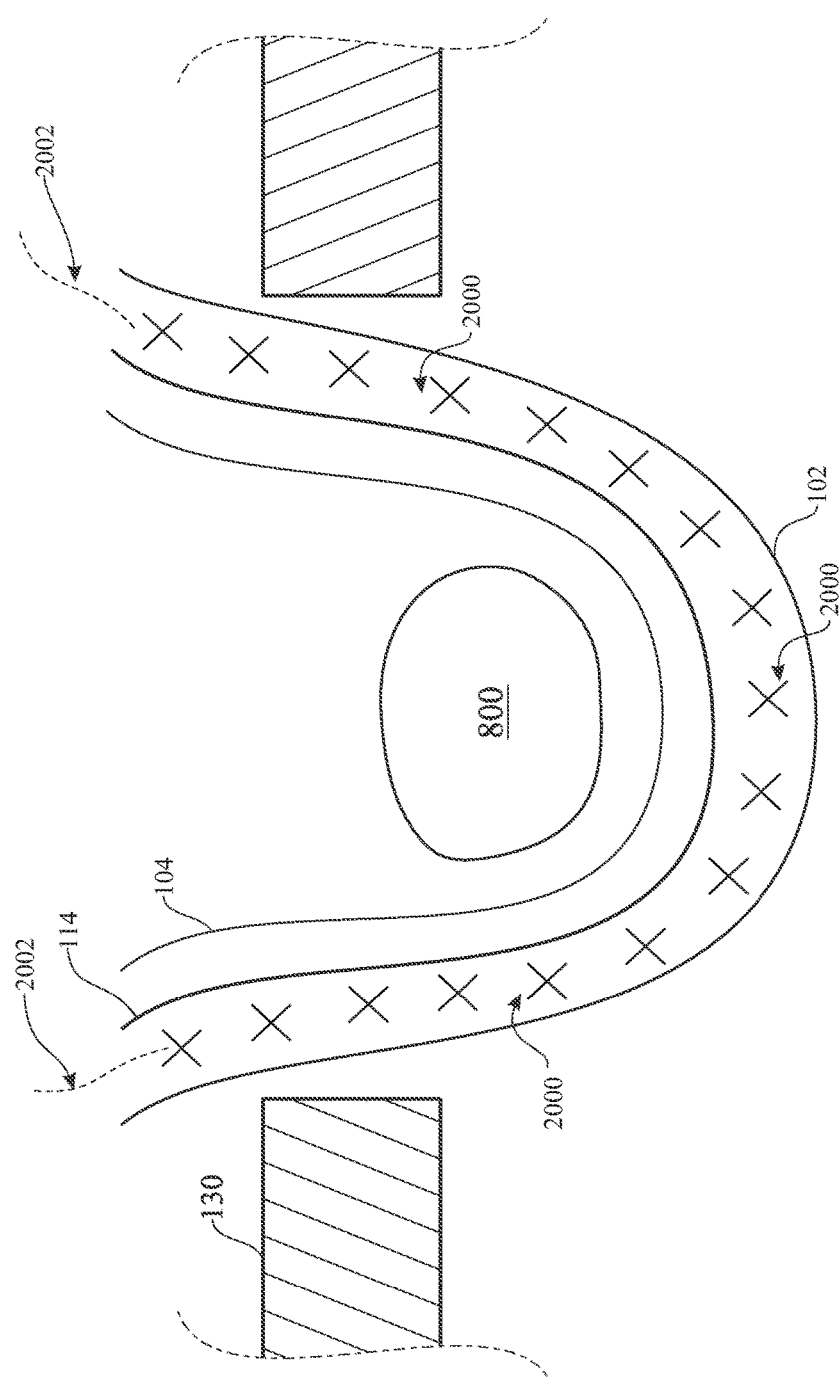
FIG. 20 presents a cross sectional side view of an exemplary contained tissue extraction device including a wire mesh bag, in accordance with aspects of the invention, the cross section taken along sectional plane 20-20 indicated in FIG. 1.

It is anticipated that a wire mesh 2000 may be included in the contained tissue extraction device 100 as shown in FIGS. 2 and 20. FIG. 2 shows the mesh 2000 in perspective and FIG. 20 shows a cross section of the mesh placed between layers (bags) of the contained tissue extraction device (e.g. the mesh may line the adjacent layers). For example, the mesh 2000 may be disposed between the wires (e.g. wire 114 of FIG. 20) and the outer bag 102 as shown in FIG. 20. The mesh may be a bag or pouch, include a drawstring 2002. The mesh and the drawstring may be configured such that when the drawstring is pulled, the mesh collapses. The mesh may include a weave pattern found in Chinese finger traps, such that when the drawstring is tightened, the mesh collapses tightly into itself. As such, the mesh may include a helical braid weave. Because of this configuration, the mesh may be tightened over a contained target tissue by a user or surgeon via pulling the drawstring 2002. The tightening of the mesh over the tissue compresses the tissue, and thus keeps the tissue from rolling around or moving during morcellation to provide cleaner, efficient, effective, and accurate slices. The wires are between the mesh 2000 and the inner layer 104. The mesh further aids in keeping the wires from cutting or puncturing the outer bag 102 since the mesh tightens away from the outer bag toward a contained tissue. The mesh may be freely disposed or unattached or unglued to the wires or the outer bag 102. However, the mesh may be lightly glued or detachably secured to the outer bag 102 in some embodiments. The mesh may be composed of any suitable material such as plastic, or nylon, and may be formed by weaved wire. It is to be understood that the mesh itself does not cut or morcellate the tissue, and is included to maintain compression on the tissue during morcellation (e.g. when the wires are being pulled out or oscillated to saw through or cut the tissue).

As described above, the wires may be disposed between the inner bag 104 and the outer bag 102. A first set of wires may be placed in parallel directly adjacent an outside surface of the inner bag as shown in FIG. 2 where the wires (e.g. plurality of wires 114) are spaced apart and run parallel along an outer surface of the inner bag 104 so that they do not cross each other. An additional second wire or set of wires may be included that are disposed perpendicular to the first set of wires. For example, FIG. 2 shows a perpendicular wire 207 disposed perpendicularly relative to the longitudinal directions or extensions of the wires (e.g. wire 114). A plurality of such a perpendicular wire 207 (e.g. second set of wires) may be included, and the set of perpendicular wires 207 may be parallel with one another. As such, once assembled, a surgeon may first remove the first set of wires (e.g. wire 114) and then after the first set is removed, the surgeon may begin to remove the second set of wires (e.g. perpendicular wire 207), causing the tissue to be morcellated in a crossed pattern (e.g. with crossing morcellating planes). It is to be understood that an additional layer may be placed between the perpendicular wire 207 and the first set of wires (114), however the device may in some embodiments have the perpendicular wire 207 and the first set of wires 114 touching.

The inner bag 104 may be glued to the outer bag 102 to sandwich the wires between the inner hag 104 and the outer bag 102. The inner and outer bags may be glued such that the wires are not glued, and such that the wires may slide freely in pockets 107 (FIG. 1) formed by gluing the inner and outer bag together over the wires. As such the wires may be loosably placed between the inner and outer bag. As such, glue may be only applied to areas of the bags (to glue the bags together) that are not in contact with the wires. For example, only portions of the bags that outlie morcellating planes and wires may be glued together to allow the wires to slide freely along grooves or pockets 107. As such, gluing the inner and outer bag together forms a set of pockets 107 that guide the free-sliding wires during morcellation. Such pockets may work in conjunction with the herein described engagement routes. The wires may be lightly glued to the inner bag or the outer bag to keep them in place during transport or handling, but to allow the wires to separate from surfaces they are glued to easily. It is to be understood that the pockets may contain the wire segments.

The wires may include one or more tissue abrasive snags 307 as shown in FIG. 3. The tissue abrasive snag 307 is a bump, projection, or bit that is configured to aid in morcellating the tissue when the wires are pulled back and forth. For example, the snag 307 may include projections 311 that are configured to slice or cut a tissue but not puncture or slice the outer bag 102. In embodiments where the wires are smooth, the snag 307 is configured to tear, cut, scrape, or slice a target tissue upon pulling the wires back and forth at the wire ends 108 as described herein (e.g. while keeping the wire tight around the target tissue).

Figure 18:
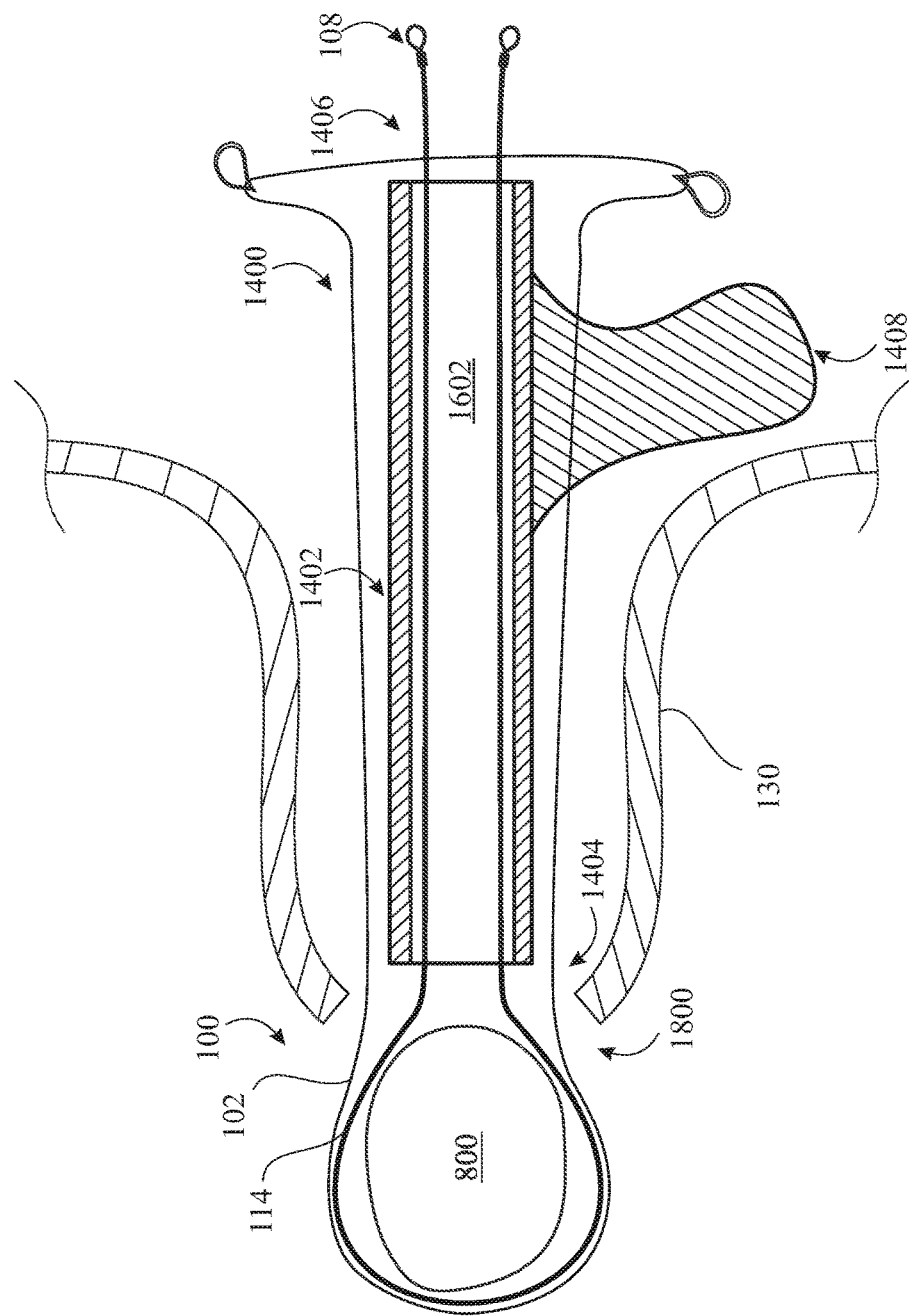
FIG. 18 presents a cross sectional side view of the guide tool of used in a vaginal canal with a contained tissue extraction bag, in accordance with aspects of the invention.
Figure 19:
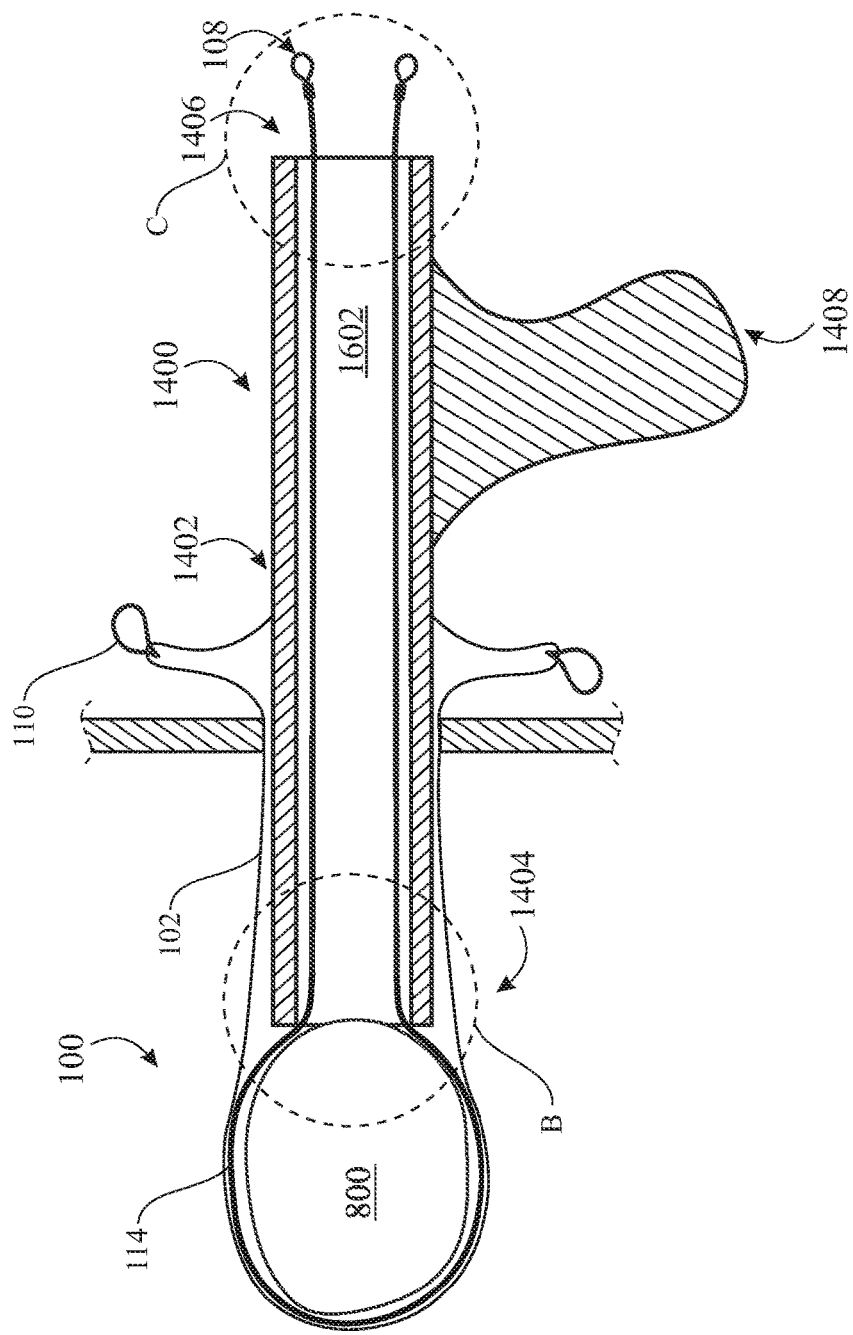
FIG. 19 presents a cross sectional side view of the guide tool and a contained tissue extraction bag used together, where a front end of the guide tool is placed inside an intracorporeal cavity and inside a contained tissue extraction bag, such that the front end contacts a target tissue captured inside the contained tissue extraction bag, in accordance with aspects of the invention.
Figure 19A:
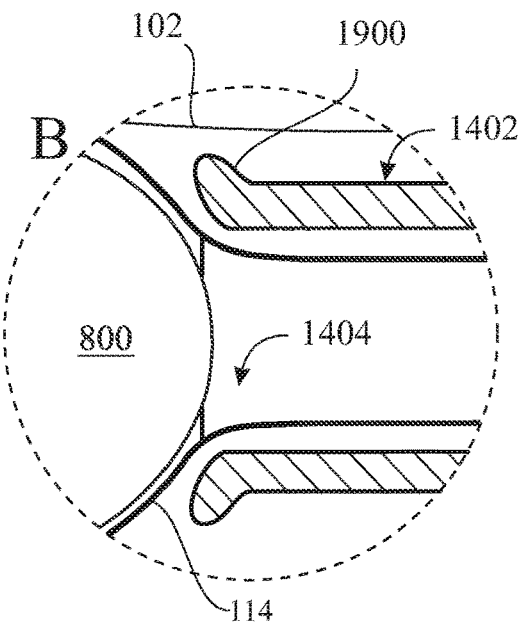
FIGS. 19A and 19B are zoomed in views of sections B and C indicated in FIG. 19, showing the guide tool in more detail, in accordance with aspects of the invention.
Figure 19B:
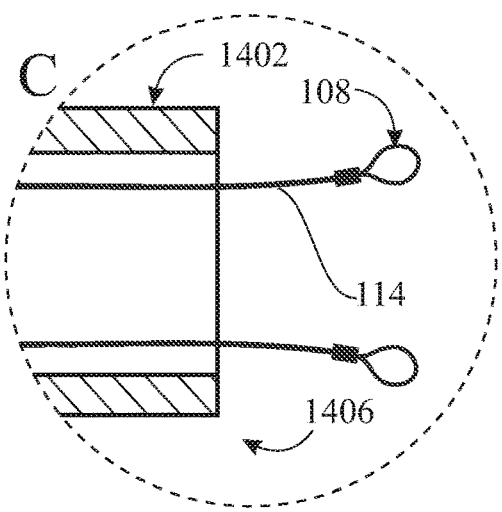

The illustrations of FIGS. 14-19, and 19A and 19B show an exemplary wire guide 1400 allowing a user to thread two ends of the wires through the wire guide to keep the wires from damaging surrounding tissue of an incision or opening through which the contained tissue extraction device is operating. For example, the wire guide 1400 includes a barrel 1402, a front end 1404, a back end 1406, a handle 1408, and a bore 1602 defined by the barrel 1402. The bore extends from the front end to the back end, and may be cylindrical. As can be seen in the figures, and more particularly in FIG. 19, the front end of the wire guide may be inserted into an incision where a target tissue 800 is being contained by the disclosed contained tissue extraction device. As such, the front end of the wire guide is inserted into a mouth of the contained tissue extraction device and its respective bags such that the front end contacts the target tissue. The wires ends 108 may be threaded through the bore 1602 (e.g. the bore receives the wires and the wire ends) while the front end of the wire guide is brought closer to the target tissue to ultimately cause the front end of the wire guide to contact the target tissue. As such the wires may be pulled tight (via pulling wire ends 108) around the target tissue while remaining threaded through the bore, and while the front end contacts the target tissue. Such configuration protects tissue in the vicinity of an incision since the barrel keeps the wires from contacting the surrounding tissue. As seen in FIG. 19A, the front end of the barrel may include a curved portion 1900 configured to allow the wires to pass through the bore without getting caught or snagging on the front end of the barrel. The wires may morcellate a tissue as described above while being threaded through the wire guide (e.g. both ends completely through the front and back end). FIG. 18 shows the wire guide being used with the disclosed contained tissue extraction bags in a vaginal canal 1800. Since the barrel protects surrounding tissues from the wires that are threaded through the barrel, the wire guide provides safety to surrounding tissues (e.g. around a vicinity of an incision) during the morcellation of tissues located in elongated cavities. The wire guide 1400 may have various dimensions. For example, the barrel may have a length of 25 cm, a diameter/width of 8 mm or 1 cm, and the handle may have a length of 10 cm. It is to be understood that the wire guide may be provided with the above described bag in a kit.

In conclusion, disclosed is a contained tissue extraction device that allows a surgeon to safely morcellate a tissue inside an intracorporeal cavity such that the tissue does not disseminate to other areas of a patient's body. Further, the disclosed contained tissue extraction device allows morcellation of a tissue into clean-cut segments, solving the problem of inaccurate screening of paste-like tissue that may result from traditional morcellator devices.

Since many modifications, variations, and changes in detail can be made to the described preferred embodiments of the invention, it is intended that all matters in the foregoing description and shown in the accompanying drawings be interpreted as illustrative and not in a limiting sense.

Thus, the scope of the invention should be determined by the appended claims and their legal equivalents.

What is claimed is:

1. A tissue extraction device for being introduced into an incision to an intracorporeal region and for capturing and morcellating a target tissue of the intracorporeal region, the device comprising:
    a non-permeable outer bag, the outer bag having a mouth;
    an inner bag lining the outer bag;
    a set of wire segments placed between the inner bag and the outer bag, the wire segments having ends that are disposed near the mouth;
    wherein each wire segment of the set of wire segments is arranged to be separately removable from their placement between the bags; and
    wherein the outer bag is tightenable around the target tissue by pulling the mouth out of the incision to a tightened configuration, and in the tightened configuration, the ends are motionable to cause the wire segments to pass through the inner bag to begin morcellating the target tissue.

2. The tissue extraction device of claim 1, wherein the set of wire segments is sandwiched between the inner bag and the outer bag, the inner bag and the outer bag being glued together to form a set of pockets between the inner bag and the outer bag where the inner bag and the outer bag contact the wire segments.

3. The tissue extraction device of claim 1, wherein the wire segments are loosably placed between the inner bag and the outer bag.

4. The tissue extraction device of claim 1, wherein the wire segments have a serrated finish configured to saw through the target tissue when the ends are motioned back and forth in the tightened configuration.

5. The tissue extraction device of claim 1, wherein the device includes a wire guide including a barrel, the barrel configured to receive one or more ends of the wire segments such that the wire segments may be threaded through the bore before being motioned.

6. The tissue extraction device of claim 1, wherein the device further comprises a mesh bag between the wire segments and the outer bag, the mesh configured to collapse and compress the target tissue when a drawstring of the mesh bag is pulled.

7. The tissue extraction device of claim 1, wherein the wire segments include a tissue abrasive snag configured to cut the target tissue.

8. The tissue extraction device of claim 1, wherein the wire segments are smooth.

9. The tissue extraction device of claim 1, wherein the device further comprises indicators for indicating a sequence in which the ends of the wire segments are to be motioned to morcellate the target tissue.

10. The tissue extraction device of claim 1, wherein the device further comprises a protective sleeve disposed between the wire segments and the outer bag.

11. A tissue extraction device for being introduced into an incision to an intracorporeal region and for capturing and morcellating a target tissue of the intracorporeal region, the device comprising:
    a non-permeable outer bag, the outer bag having a mouth;
    an inner bag lining the outer bag;
    a set of wire segments placed between the inner bag and the outer bag, the wire segments having ends that are disposed near the mouth;
    wherein each wire segment of the set of wire segments is arranged to be separately removable from their placement between the bags and wherein the set of wire segments is sandwiched between the inner bag and the outer bag, the inner bag and the outer bag being glued together at areas between the wire segments to form a set of pockets between the inner bag and the outer bag, the pockets containing the wire segments; and wherein the outer bag is tightenable around the target tissue by pulling the mouth out of the incision to a tightened configuration, and in the tightened configuration, the ends are motionable to cause the wire segments to pass through the inner bag to begin morcellating the target tissue.

12. The tissue extraction device of claim 11, wherein the wire segments are loosably placed between the inner bag and the outer bag.

13. The tissue extraction device of claim 11, wherein the wire segments have a serrated finish configured to saw through the target tissue when the ends are motioned back and forth in the tightened configuration.

14. The tissue extraction device of claim 11, wherein the device includes a wire guide including a barrel, the barrel configured to receive one or more ends of the wire segments such that the wire segments may be threaded through the bore before being motioned.

15. The tissue extraction device of claim 11, wherein the device further comprises a mesh between the wire segments and the outer bag, the mesh configured to collapse and compress the target tissue when a drawstring of the mesh is pulled.

16. The tissue extraction device of claim 11, wherein the wire segments are smooth and are attachable to serrated wire segments such that one end of each wire segment is pullable away from the mouth of the outer bag to guide the serrated wire segments to engage and morcellate the target tissue.

17. The tissue extraction device of claim 11, wherein the wire segments are composed of nylon and are thin enough to be pulled through the target tissue.

18. The tissue extraction device of claim 11, wherein the device further comprises indicators for indicating a sequence in which the ends of the wire segments are to be motioned to morcellate the target tissue.

19. The tissue extraction device of claim 11, wherein the device further comprises a protective sleeve disposed between the wire segments and the outer bag.

* * * * *